(12) United States Patent
Sasaki et al.

(10) Patent No.: US 12,409,431 B2
(45) Date of Patent: Sep. 9, 2025

(54) GUAR GUM MICROCAPSULES

(71) Applicant: International Flavors & Fragrances Inc., New York, NY (US)

(72) Inventors: Takashi Sasaki, Union Beach, NJ (US); Lewis Michael Popplewell, Union Beach, NJ (US); Ronald Gabbard, Union Beach, NJ (US); Ryan Chin, Union Beach, NJ (US); Yabin Lei, Union Beach, NJ (US); Julie Ann Wieland, Union Beach, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 813 days.

(21) Appl. No.: 17/416,080

(22) PCT Filed: Dec. 17, 2019

(86) PCT No.: PCT/US2019/066816
§ 371 (c)(1),
(2) Date: Jun. 18, 2021

(87) PCT Pub. No.: WO2020/131855
PCT Pub. Date: Jun. 25, 2020

(65) Prior Publication Data
US 2022/0040658 A1 Feb. 10, 2022

Related U.S. Application Data

(60) Provisional application No. 62/781,162, filed on Dec. 18, 2018.

(51) Int. Cl.
| | |
|---|---|
| *B01J 13/16* | (2006.01) |
| *A61K 8/11* | (2006.01) |
| *A61K 8/34* | (2006.01) |
| *A61K 8/37* | (2006.01) |
| *A61K 8/44* | (2006.01) |
| *A61K 8/73* | (2006.01) |
| *A61K 8/92* | (2006.01) |
| *A61K 9/50* | (2006.01) |
| *A61Q 5/02* | (2006.01) |
| *A61Q 5/12* | (2006.01) |
| *A61Q 13/00* | (2006.01) |
| *A61Q 15/00* | (2006.01) |
| *A61Q 19/00* | (2006.01) |
| *A61Q 19/10* | (2006.01) |
| *B01J 13/20* | (2006.01) |
| *C08G 18/64* | (2006.01) |
| *C08G 18/70* | (2006.01) |
| *C08K 5/07* | (2006.01) |

(Continued)

(52) U.S. Cl.
CPC ............... *B01J 13/16* (2013.01); *A61K 8/345* (2013.01); *A61K 8/375* (2013.01); *A61K 8/44* (2013.01); *A61K 8/73* (2013.01); *A61K 8/731* (2013.01); *A61K 8/736* (2013.01); *A61K 8/922* (2013.01); *A61K 9/5047* (2013.01); *A61K 9/5089* (2013.01); *A61Q 5/02* (2013.01); *A61Q 5/12* (2013.01); *A61Q 15/00* (2013.01); *A61Q 19/007* (2013.01); *A61Q 19/10* (2013.01); *B01J 13/206* (2013.01); *C08G 18/6484* (2013.01); *C08G 18/705* (2013.01); *C08K 5/07* (2013.01); *C11D 3/001* (2013.01); *C11D 3/0015* (2013.01); *A61K 8/11* (2013.01); *A61Q 13/00* (2013.01); *C11D 3/505* (2013.01); *C11D 2111/12* (2024.01)

(58) Field of Classification Search
CPC ......... B01J 13/16; B01J 13/206; A61K 8/345; A61K 8/375; A61K 8/44; A61K 8/73; A61K 8/731; A61K 8/736; A61K 8/922; A61K 9/5047; A61K 9/5089; A61K 8/11; A61Q 5/02; A61Q 5/12; A61Q 15/00; A61Q 19/007; A61Q 19/10; A61Q 13/00; C08G 18/6484; C08G 18/705; C08K 5/07; C11D 3/001; C11D 3/0015; C11D 2111/12; C11D 3/505
See application file for complete search history.

(56) References Cited

U.S. PATENT DOCUMENTS

| | | |
|---|---|---|
| 8,449,918 B2 | 5/2013 | Lapidot et al. |
| 9,532,933 B2 | 1/2017 | Lei et al. |

(Continued)

FOREIGN PATENT DOCUMENTS

| | | |
|---|---|---|
| WO | 2007101059 A2 | 9/2007 |
| WO | 2017001385 A1 | 1/2017 |
| WO | 2017004339 A1 | 1/2017 |

OTHER PUBLICATIONS

Rojas, J. (2015). Improved Polymer Functionality by Cross-linking with Glutaraldehyde to Achieve Controlled Drug Release. In: Narang, A., Boddu, S. (eds) Excipient Applications in Formulation Design and Drug Delivery. Springer, Cham. https://doi.org/10.1007/978-3-319-20206-8_19 (Year: 2015).*

(Continued)

*Primary Examiner* — Doan T Phan

(57) ABSTRACT

Disclosed are microcapsule compositions having a microcapsule that contains a microcapsule core and a microcapsule shell encapsulating the microcapsule core. The microcapsule has a particle size of 1 micron to 100 microns in diameter. The microcapsule core contains an active material. The microcapsule shell is formed of at least three moieties, in which a first moiety is derived from a polygalactomannan, a second moiety is derived from a polyisocyanate, and a third moiety is derived from a multi-functional aldehyde or a tannic acid.

13 Claims, No Drawings

(51) Int. Cl.
*C11D 3/00* (2006.01)
*C11D 3/50* (2006.01)

(56) References Cited

U.S. PATENT DOCUMENTS

| | | | |
|---|---|---|---|
| 9,993,401 B2 | 6/2018 | Barnett et al. | |
| 2011/0033513 A1 | 2/2011 | Lei et al. | |
| 2014/0106032 A1 | 4/2014 | Dardelle et al. | |
| 2015/0017214 A1* | 1/2015 | Warr | A61Q 17/04 510/438 |
| 2015/0132377 A1* | 5/2015 | Reymar | A61Q 13/00 424/463 |
| 2015/0250689 A1* | 9/2015 | Dardelle | C11D 3/505 264/4.1 |
| 2016/0158121 A1 | 6/2016 | Lei et al. | |
| 2016/0193122 A1 | 7/2016 | Lei et al. | |
| 2018/0042825 A1* | 2/2018 | Lei | A61K 8/84 |
| 2018/0369777 A1* | 12/2018 | Shi | B01J 13/16 |
| 2019/0177505 A1* | 6/2019 | Guskey | A61K 8/87 |
| 2020/0306197 A1 | 10/2020 | Brahms et al. | |

OTHER PUBLICATIONS

George et al. "pH sensitive alginate-guar gum hydrogel for the controlled release of protein drugs." International Journal of Pharmaceutics, 2007, 335: 123-129. (Year: 2007).*
International Preliminary Report on Patentability in PCT/US2019/066816, dated Jun. 16, 2021.
International Search Report and Written Opinion in PCT/US2019/066816, dated Apr. 24, 2020.
Office Communication dated Feb. 26, 2021 in U.S. Appl. No. 16/086,198, filed Mar. 20, 2017.

* cited by examiner

GUAR GUM MICROCAPSULES

CROSS-REFERENCE TO RELATED APPLICATIONS

This application is a 37 U.S.C 371 national stage of International Application No. PCT/US2019/066816, filed Dec. 17, 2019, which claims priority to U.S. Application Ser. No. 62/781,162 filed Dec. 18, 2018. The contents of all applications are incorporated by reference in their entirety.

BACKGROUND

Consumers prefer environment friendly products over synthetic polymers. Conventional delivery systems are widely used in consumer products for releasing a fragrance or flavor to a target area in a controlled manner. The delivery systems are particularly useful for fragrance delivery, which typically utilizes microcapsules formed of synthetic polymers such as melamine formaldehyde, polyurea, or polyacrylate.

Microcapsules prepared from natural materials have been reported in Mint et al., WO2016185171, with a fungal chitosan. However, Mint et al. does not include fragrance performance results. Silk fibroin particles have also been used to encapsulate fragrance oil. See Kaplan et al., US20150164117A1. No performance benefit has been reported in consumer products. U.S. Pat. No. 4,946,624A describes gelatin microcapsules, which only has a modest fragrance performance. These gelatin microcapsules are not good enough for consumer products such as fabric softeners.

There is a need to develop environment friendly microcapsules with a high fragrance performance for use in laundry, washing, cleaning, surface care and personal and skin care.

SUMMARY OF THE INVENTION

This invention is based on the discovery that certain capsule compositions possess unexpected desirable properties such as high perceived olfactory intensity and biodegradability.

Accordingly, one aspect of this invention relates to a microcapsule composition containing a plurality of microcapsules, in which each microcapsule has a microcapsule core and a microcapsule shell encapsulating the microcapsule core, and the microcapsule shell, having an inner surface and an outer surface, is formed of a reaction product of at least three monomers, in which a first monomer is a polygalactomannan (e.g., a cationic guar gum, a native guar gum, a hydroxypropyl guar gum, guar hydroxypropyltrimonium chloride), a second monomer is a polyisocyanate, and a third monomer is a multi-functional aldehyde. The microcapsule is formed from an emulsion having oil drops suspended in an aqueous phase. The interface is formed of one or more anionic emulsifier, preferably of natural or naturally derived origin. Optionally, one or more water or oil dispersible polyisocyanates constitute 0.01% to 10% by weight of the microcapsule composition. Preferably, the microcapsule composition contains 0.01% to 10% of one or more water dispersible multi-functional aldehydes.

The cationic guar includes, but are not limited to, commercially available cationic guars such as those under the trademarks of N-Hance™ 3000, N-N-Hance™ 3196, N-Hance™ 4572, N-Hance™ C261N, N-Hance™ BF13, N-Hance™ CG13, N-Hance™ 3215, N-Hance™ HPCG 1000, N-Hance™ CGC 45, Aquacat™ PF618, Aquacat™ CG518, (all of which are manufactured by Ashland); Dehyquart® N, Dehyquart® TC, and Dehyquart® HP, from BASF; Activsoft™ C-13, Activisoft C-14, and Activisoft™ C-17, from Innospec; Ecopol™-13, Ecopol™-14, Ecopol™-17, Ecopol™-261, by Economy Polymer & Chemicals; Guar 13S, Guar 14S, Guar 15S, Guarquat C130KC (guar hydroxypropyltrimonium chloride), Guarquat C140KC, Guarquat L80KC, Jaguar® C-14-S, Jaguar® C-17, Jaguar® C-500, Jaguar® Excel, Jaguar® Optima, SPI-6520, SPI-7006, SPI-7010, SPI-7010LV, Vida-Care™ GHTC 03, Vida-Care™ GHTC 04, iQUAT™ GUAR 14S, iQUAT™ GUAR CLEAR NT500, and the like.

The details of one or more embodiments of the invention are set forth in the description below. Other features, objects, and advantages of the invention will be apparent from the description and the claims.

DETAILED DESCRIPTION OF THE INVENTION

It has been found that certain guar-containing microcapsules have unexpectedly high fragrance performance and are environment friendly. These guar microcapsule compositions have been successfully incorporated into many consumer applications.

Exemplary applications include personal hair care products such as shampoos and hair conditioners; personal washes such as soaps, body wash, personal cleaners, and sanitizers; fabric care such as fabric refreshers, softeners, and dryer sheets; ironing water; industrial cleaners; liquid and powder detergent; rinse conditioners; fine fragrances; an Eau De Toilette product; a deodorant; a roll-on product; and an aerosol product. The microcapsule composition of this invention can be added to a consumer product base directly or be printed onto a product base or a movable product conveyor (e.g., a non-stick belt) for drying. See International Application Publication WO2019212896A1. In a typical printing system, the microcapsule composition is printed onto a movable product conveyor that directly receives the printed microcapsule, which is then dried on the movable product conveyor to produce a dried product. Additional carriers and solvent can be added to the microcapsule composition before printing. In some embodiments, the viscosity of the microcapsule composition is adjusted to more than 500 centipoise (cP) or more than 1000 cP with a viscosity modifier. With reference to the print assembly, the print assembly can include a print head or array of nozzles and optionally be adapted to print the microcapsule in a dot pattern (e.g., arranged to facilitate drying, post-processing, and product quality). Optional features of the system include, a dehumidifier configured to supply desiccated air to the drying component; a supplemental energy source (e.g. a radiant heat source), for facilitating drying of the printed microcapsule; and/or a product discharge component for removing dried product from the movable product conveyor.

The microcapsule compositions of this invention each have a microcapsule dispersed in an aqueous phase. The microcapsule contains a microcapsule core and a microcapsule shell encapsulating the microcapsule core. The microcapsule core contains an active material (e.g., a fragrance). The microcapsule shell is formed of at least three moieties, in which a first moiety is derived from a polygalactomannan, a second moiety is derived from a polyisocyanate, a third moiety is derived from a multi-functional aldehyde or a tannic acid, Preferably, the third moiety is derived from the tannic acid, and a fourth moiety is derived from the multi-functional aldehyde. The microcapsule composition can further contain an emulsifier, such as an octenyl succinic anhydride (OSA)-modified starch, OSA modified gum acacia, gum acacia, alginate, carboxylmethylcellulose, carageenan, xanthan gum, gellan gum, lecithin, modified lecithin, protein, modified protein, pectin, modified pectin, lignin, modified lignin, and combinations thereof. The polyisocyanate is usually present at a level of 0.01% to 10% by weight of the microcapsule composition. Examples include a trimer of hexamethylene diisocyanate, a trimer of isophorone diisocyanate, a biuret of hexamethylene diisocyanate, a polyisocyanurate of toluene diisocyanate, a trimethylol propane-adduct of toluene diisocyanate, a trimethylol propane-adduct of xylylene diisocyanate, or a combination thereof. The multi-functional aldehyde can be present at a level of 0.01% to 10% by weight of the microcapsule composition. Preferred multi-functional aldehydes are selected from the group consisting of glutaraldehyde, glyoxal, di-aldehyde starch, malondialdehyde, genipin, and combinations thereof. The microcapsule shell optionally contains an amino moiety derived from a polyamine selected from the group consisting of lysine, poly-lysine, hexamethylene diamine, branched polyethylenimine, polyvinylamine, guanidine, guanidine salts, 3,5-diamino-1,2,4-triazole, chitin, chitosan, and combinations thereof. In some embodiments, the polygalactomannan is covalently bonded to the multi-functional aldehyde via one or more acetal or hemiacetal bonds.

Nonlimiting active materials include a pro-fragrance, flavor, malodor counteractive agent, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, nanometer to micron size inorganic solid, polymeric or elastomeric particle, taste modulator, cell, probiotic, and combinations thereof The microcapsule compositions in some embodiments also have a deposition polymer selected from the group consisting of trimonium, methacrylamidopropyl trimethyl ammonium, chitosan, acrylamidopropyl trimethylammonium, acrylamide, acrylic acid, dimethyl ammonium, xlylose, galactose, hydroxypropylated glucose, hydroxyethylated glucose, hydroxymethylated glucose, vinylamine, ethylenimine, functionalized branched polyethylenimine, vinylformamide, vinylpyrollidone, caprolactone, catechol, vinylalcohol, polyquaternium-4, polyquaternium-5, polyquaternium-6, polyquaternium-7, polyquatemium-10, polyquatemium-11, polyquaternium-16, polyquaternium-22, polyquaternium-24, polyquaternium-28, polyquaternium-37, polyquatemium-39, polyquaternium-44, polyquaternium-46, polyquaternium-47, polyquaternium-53, polyquatemium-55, polyquaternium-67, polyquatemium-68, polyquaternium-69, polyquaternium-73, polyquaternium-74, polyquaternium-77, polyquaternium-78, polyquaternium-79, polyquaternium-79/hydrolyzed keratin, polyquaternium-80, polyquatemium-81, polyquaternium-82, polyquatemium-86, polyquatemium-88, polyquatemium-101, polyvinylamine, polyethyleneimine, a copolymer of vinylamine and vinylformamide, a copolymer of acrylamide and 3-methacryloylaminopropyl trimethylammonium, a 3-acrylamidopropyl trimethylammonium polymer or its copolymer, a diallyldimethylammoniumchloride polymer and its copolymer, a polysaccharide with saccharide unit functionalized with hydroxypropyl trimmonium, ethyltrimonium chloride methacrylate/hydrolyzed wheat protein copolymer, alkyl-monium hydroxypropyl hydrolyzed protein and combinations thereof.

Also within the scope of the invention are consumer products containing any of the microcapsule compositions described above. Exemplary consumer products are a baby care product, a diaper rash cream or balm, a baby powder, a diaper, a bib, a baby wipe, a cosmetic preparation, a powder foundation, a liquid foundation, an eye shadow, a lipstick or lip balm, a home care product, an all-purpose cleaner, a scent drop product, a bathroom cleaner, a floor cleaner, a window cleaner, a plastics polish, a bleach, a toilet cleaner, a toilet rimblock, a bath tissue, a paper towel, a disposable wipe, liquid air freshener, air freshener spray, a spray dispenser product, an incense stick, a rug deodorizer, a candle, a room deodorizer, a liquid dish detergent, an automatic dish detergent, a powder dish detergent, a leather detergent, a tablet dish detergent, a paste dish detergent, a unit dose tablet or capsule, a flavor, a beverage flavor, a diary flavor, a fruit flavor, a miscellaneous flavor, a sweet goods flavor, a tobacco flavor, a toothpaste flavor, a chewing gum, a breath freshener, an orally dissolvable strips, a chewable candy, a hard candy, an oral care product, a tooth paste, a toothbrush, a dental floss, an oral rinse, an tooth whitener, a denture adhesive, a health care device, a tampon, a feminine napkin, an anti-inflammatory balm, an anti-inflammatory ointment, an anti-inflammatory spray, a disinfectant, a personal care product, a soap, a bar soap, a liquid soap, a bath fragrance, a body wash, a non-aerosol body spray, a body milk, a cleanser, a body cream, a hand sanitizer, a hand wash, a functional product base, a sunscreen lotion, a sunscreen spray, a deodorant, an anti-perspirant, an roll-on product, an aerosol product, a natural spray product, a wax-based deodorant, a glycol type deodorant, a soap type deodorant, a facial lotion, a body lotion, a hand lotion, a miscellaneous lotion, a body powder, a shave cream, a shave gel, a shave butter, a bath soak, a shower gel, an exfoliating scrub, a foot cream, a facial tissue, a cleansing wipe, a talc product, a hair care product, a hair care with ammonia, a shampoo, a hair conditioner, a hair rinse, a hair refresher, a hair fixative or styling aid, a hair bleach, a hair dye or colorant, a fabric care product, a fabric softener, a liquid fabric softener, a fabric softener sheet, a drier sheet, a fabric refresher, an ironing water, a detergent, a laundry detergent, a liquid laundry detergent, a powder laundry detergent, a tablet laundry detergent, a laundry detergent bar, a laundry detergent cream, a hand wash laundry detergent, a scent booster, a fragrance, a cologne, compounds, an encapsulated fragrance, a fine fragrance, a men's fine fragrance, a women's fine fragrance, a perfume, a solid perfume, an Eau De Toilette product, a natural spray product, a perfume spray product, an insect repellent product, and a wildlife scent. Preferred products are shampoos, hair conditioners, bar soaps, shower gels, detergents, fabric conditioners or softeners, fabric refreshers, scent-boosters, antiperspirants, bodyspray/mist, lotions, candles, or textile products.

In a preferred embodiment, the microcapsule wall is formed of an encapsulating polymer contains a moiety of a cationic guar. The wall has an inner surface and outer surface. The inner surface is in contact with the microcapsule core. The outer surface is in contact with the environment where the microcapsule resides, e.g., a water phase, skin, and hair.

The microcapsules of this invention each have a particle size (in diameter) of 0.1 microns to 1000 microns (e.g., 0.5 microns to 500 microns, 1 micron to 200 microns, and 1 micron to 100 microns) with a lower limit of 0.1 microns, 0.5 microns, 1 micron, 2 microns, and 5 microns and an upper limit of 1000 microns, 500 microns, 200 microns, 100 microns, 75 microns, 50 microns, and 30 microns.

The microcapsules can be positively or negatively charged with a zeta potential in the range of −200 mV to +200 mV, e.g., at least 10 mV, 25 mV or greater, 40 mV or greater, 25 mV to 200 mV, and 40 mV to 100 mV, with a lower limit of −200 mV, −150 mV, −100 mV, −50 mV, −25 mV, −10 mV, 0 mV, 10 mV, 20 mV, and 40 mV and an upper limit of 200 mV, 150 mV, 100 mV, 50 mV, 40 mV, 20 mV, 10 mV, 0 mV, −10 mV, and −25 mV. Preferably, the microcapsules each are positively charged. Not to be bound by theory, the positively charged microcapsules have a strong affinity to specific animate and inanimate surfaces (e.g., hair and fabric), and also are unexpectedly stable in certain consumer product bases such as hair conditioners, shampoos, shower gels, and fabric conditioners.

The microcapsule compositions of this invention can be prepared by the steps of:
(a) provide an aqueous phase containing a polygalactomannan (e.g., a cationic guar gum) and an anionic emulsifier,
(b) providing an oil phase containing a polyisocyanate and an active material,
(c) emulsifying the aqueous phase into the oil phase form an oil-in-water emulsion,
(d) optionally adding a polyisocyanate or aldehyde,
(e) adjusting the pH to below 8 (e.g., below 7, and between 1 and 6),
(f) causing the formation of a microcapsule having a microcapsule core that contains the active material and a microcapsule wall that encapsulates the microcapsule core,
(g) curing the microcapsule to obtain a guar microcapsule dispersed in the aqueous phase, e.g., at a temperature of 40 to 250° C. for 5 minutes to 48 hours.

Optionally, the method includes one or more steps of (i) washing the microcapsule with water, (ii) adding lysine, poly-lysine, hexamethylene diamine, branched polyethylenimine, polyvinylamine, guanidine, guanidine salts, 3,5-diamino-1,2,4-triazole, chitin, chitosan, or any combination thereof, (iii) spray drying or removing the water from the microcapsule slurry, or after the curing step, adding a chitosan aqueous solution to 0.5% to 5% by weight of the microcapsule composition at a pH of 1 to 5, and heating the resultant mixture to 35° C. to 95° C. (e.g., 40° C. to 75° C., for a period of 5 minutes to 10 hours or 2 hours to 6 hours).

The microcapsule of this invention can also be prepared by printing a microcapsule shell and a microcapsule core using a printing system such as a 3D printer. See WO2016172699A1. Suitable active materials for printing include fragrances, flavors, malodor counteractive agents, cosmetic actives, and nutrients. The printing steps generally include depositing the active materials and the microcapsule shell material in a layer-by-layer fashion, preferably through separate printer heads. The microcapsule shell material can be polymers containing a polygalactomannan or oil-in-water emulsions as described above.

The microcapsule compositions are biodegradable. "Biodegradable" as used herein with respect to a material, such as a microcapsule as a whole and/or a biopolymer of the microcapsule shell, has no real or perceived health and/or environmental issues, and is capable of undergoing and/or does undergo physical, chemical, thermal, microbial and/or biological degradation. Ideally, a microcapsule and/or biopolymer is deemed "biodegradable" when the microcapsule and/or biopolymer passes one or more of the Organization for Economic Co-operation and Development (OECD) tests including, but not limited to OECD 301/310 (Ready biodegradation with 60% or more degradation in 28 days or 60 days), OECD 302 (inherent biodegradation with 70% or more biodegradation in 7 days or 14 days), the International Organization for Standardization (ISO) 17556 (solid stimulation studies with 90% or more biodegradation relative to reference in 6 months soil), ISO 14851 (fresh water stimulation studies with 90% or more biodegradation relative to reference in 24 months in water), ISO 18830 (marine sediment stimulation studies with 90% or more biodegradation relative to reference in 24 months in water), OECD 307 (soil stimulation studies with a half life $t_{1/2}$ 180 days or less), OECD 308 (sediment stimulation studies with a half life $t_{1/2}$ 180 days or less), and OECD 309 (water stimulation studies with a half life $t_{1/2}$ 60 days or less). The composition is deemed biodegradable if it passes other testing methods such as ASTM D5988 and ASTM D5210.

In particular embodiments, the microcapsules are readily biodegradable as determined using the OECD 310 test. The pass level for ready biodegradability under OECD 310 is 60% of $CO_2$ production is reached within the 60-day period of the test.

Materials used for preparing the microcapsule composition of this invention are described in detail below.

Polygalactomannans

The polygalactomannans are polysaccharides composed principally of galactose and mannose units and are usually found in the endosperm of leguminous seeds, such as guar, locust bean, honey locust, flame tree, and the like.

Cationic polygalactomannans are especially suitable for use in the invention include polygalactomannans, such as guars, and polygalactomannan derivatives, such as hydroxyalkyl guars (for example hydroxyethyl guars or hydroxypropyl guars), that have been cationically modified by chemical reaction with one or more derivatizing agents. Derivatizing agents typically contain a reactive functional group, such as an epoxy group, a halide group, an ester group, an anhydride group or an ethylenically unsaturated group, and at least one cationic group such as a cationic nitrogen group, more typically a quaternary ammonium group. The derivatization reaction typically introduces lateral cationic groups on the polygalactomannan backbone, generally linked via ether bonds in which the oxygen atom corresponds to hydroxyl groups on the polygalactomannan backbone which have reacted. Preferred cationic polygalactomannans for use in the invention include guar hydroxypropyltrimethylammonium chlorides.

Guar hydroxypropyltrimethylammonium chlorides for use in the invention are generally comprised of a nonionic guar gum backbone that is functionalized with ether-linked 2-hydroxypropyltrimethylammonium chloride groups, and are typically prepared by the reaction of guar gum with N-(3-chloro-2-hydroxypropyl)trimethylammonium chloride.

Cationic polygalactomannans for use in the invention (preferably guar hydroxypropyltrimethylammonium chlorides) generally have an average molecular weight (weight average molecular mass (Mw) determined by size exclusion chromatography) in the range 500,000 to 3 million g/mol, more preferably 800,000 to 2.5 million g/mol.

Cationic polygalactomannans for use in the invention (preferably guar hydroxypropyltrimethylammonium chlorides) generally have a charge density of 0.5 to 1.8 meq/g.

The cationic charge density of the polymer is suitably determined via the Kjeldahl method as described in the US Pharmacopoeia under chemical tests for nitrogen determination. Specific examples of preferred cationic polygalactomannans are guar hydroxypropyltrimonium chlorides having a cationic charge density from 0.5 to 1.1 meq/g. Also suitable are mixtures of cationic polygalactomannans in which one has a cationic charge density from 0.5 to 1.1 meq/g, and one has a cationic charge density from 1.1 to 1.8 meq/g. Specific examples of preferred mixtures of cationic polygalactomannans are mixtures of guar hydroxypropyltrimonium chlorides in which one has a cationic charge density from 0.5 to 1.1 meq/g, and one has a cationic charge density from 1.1 to 1.8 meq per gram.

A particularly suitable polygalactomannan is guar gum, especially a cationic guar gum. Natural guar gum, also called guaran, is a galactomannan polysaccharide extracted from guar beans that has thickening and stabilizing properties useful in the food, feed and industrial applications. The guar seeds are mechanically dehusked, hydrated, milled and screened according to application. It is typically produced as a free-flowing, off-white powder.

The guar gum thus obtained is composed mostly of a galactomannan which is essentially a straight chain mannan (a polymer of mannose) with single membered galactose branches. The mannose units are linked in a 1-4-3-glycosidic linkage and the galactose branching takes place by means of a 1-6 linkage on alternate mannose units. The ratio of galactose to mannose in the guar polymer is therefore one to two.

A particularly useful cationic guar gum contains a hydroxypropyltrimonium group. The structure of this type of cationic guar gum is represent by the structure of Formula I:

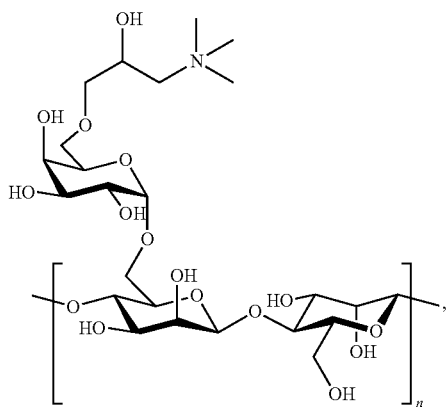

wherein n is an integer from 1 to 1,000,000 with an upper limit of 1,000,000, 500,000, 250,000, 100,000, 50,000, 25,000, 10,000, 5,000, 2,500, 1,000, 500, 250, 100, 50, 25, and 10, and a lower limit of 1, 2, 5, 10, 25, 50, 100, 250, 500, and 1000.

As used in this invention, the weight ratio between the guar gum and the aldehyde or the polyphenol is 600:1 to 3:100 (preferably 60:1 to 3:10, and more preferably 12:1 to 3:10). The weight ratio between the guar gum and the polyisocyanate is 600:1 to 3:100 (preferably 60:1 to 3:10, and more preferably 12:1 to 3:10).

Polyfunctional Nucleophile.

The polyfunctional nucleophile is optionally added to form a part of the microcapsule wall. It can be a polyfunctional amine, a polyfunctional alcohol, or a mixture thereof.

The polyamines react with a polyisocyanate or multi-functional aldehyde to form an encapsulating polymer.

Polyfunctional amines are those having at least a primary or secondary amine group (—$NH_2$ and —NH—) and one or more additional functional groups such as a primary or secondary amine and hydroxyl group (—OH). Exemplary polyfunctional amines include hexamethylene-diamine, hexaethylenediamine, ethylenediamine, 1,3-diaminopropane, 1,2-diaminopropane, 1,4-diaminobutane, diethylenetriamine, pentaethylenehexamine, bis(3-aminopropyl) amine, bis(hexanethylene)triamine, tris(2-aminoethyl) amine, triethylenetetramine, N,N'-bis(3-aminopropyl)-1,3-propanediamine, N,N,N',N'-tetrakis(2-hydroxyethyl) ethylene diamine, N,N,N',N'-tetrakis(2-hydroxypropyl) ethylene diamine, 2,4-diamino-6-hydroxypyrimidine, 2,4,6-triaminopyrimidine, tetraethylenepentamine, amino-2-methyl-1-propanol, a second branched polyethylenimine, and chitosan. Guanidine amines and guanidine salts are yet another class of multi-functional amines of use in this invention. Exemplary guanidine amines and guanidine salts include, but are not limited to, 1,3-diaminoguanidine and its monohydrochloride, 1,1-dimethylbiguanide and its hydrochloride, guanidine carbonate, and guanidine hydrochloride.

Amphoteric amines, i.e., amines that can react as an acid and a base, are another class of amines of use in this invention. Examples include proteins and amino acids such as L-lysine, D-lysine, L-arginine, D-arginine, L-lysine monohydrochloride, D-lysine monohydro-chloride, L-arginine monohydrochloride, D-arginine monohydrochloride, histidine, L-ornithine monohydrochloride, D-ornithine monohydrochloride, nisin, gelatin, and mixtures thereof.

Commercially available examples of amines include JEFFAMINE® EDR-148 (where x=2), JEFFAMINE® EDR-176 (where x=3) (from Huntsman). Other polyether amines include the JEFFAMINE® ED Series, JEFFAMINE® TRIAMINES, polyethylenimines from BASF (Ludwigshafen, Germany) under LUPASOL® grades (e.g., Lupasol® FG, Lupasol® G20 waterfree, Lupasol® PR 8515, Lupasol® WF, Lupasol® FC, Lupasol® G20, Lupasol® G35, Lupasol® G100, Lupasol® G500, Lupasol® HF, Lupasol® PS, Lupasol® HEO 1, Lupasol® PN50, Lupasol® PN60, Lupasol® P0100 and Lupasol® SK). Other commercially available polyethylenimines include EPOMIN™ P-1000, EPOMIN™ P-1050, EPOMIN™ RP18W and EPOMIN™ PP-061 from NIPPON SHOKUBAI (New York, NY). Polyvinylamines such as those sold by BASF under LUPAMINE® grades can also be used. A wide range of polyetheramines may be selected by those skilled in the art.

Polyfunctional alcohols are those having two or more hydroxyl groups. Non-limiting examples are pentaerythritol, glucose, 2-aminoethanol, dipentaerythritol, glycerol, polyglycerol, ethylene glycol, hexylene glycol, polyethylene glycol, trimethylolpropane, neopentyl glycol, sorbitol, erythritol, threitol, arabitol, xylitol, ribitol, mannitol, galactitol, fucitol, iditol, inositol, volemitol, isomalt, maltitol, lactitol, maltotriitol, maltotetraitol, polyglycitol, and combinations thereof. See WO 2015/023961 A1 for more examples of polyfunctional amines and alcohols.

The range of polyfunctional nucleophile content can vary from 0.1% to 15% (e.g., 0.2% to 10%, 0.5% to 8%, 1% to 8%, and 2% to 6%) by weight of the microcapsule. When the microcapsule is incorporated in a microcapsule composition, the polyfunctional nucleophile is present at a level of 0.05% to 8% (e.g., 0.1% to 5%, 0.1% to 4%, 0.25% to 4%, and 0.25% to 3%) by weight of the microcapsule composition.

In one embodiment, the polyfunctional nucleophile is added to the polymerization reaction at a temperature of 0-55° C. (e.g., 10-50° C., 15-45° C., 20-40° C., and 25-35° C.).

Polyfunctional Electrophiles

The polyfunctional electrophile has at least two electrophilic functional groups reactive towards the cationic guar gum or one or more of the polyfunctional nucleophiles described above. Examples of the electrophilic group include formyl, keto, carboxyl, an isocyanate group, a carboxylate ester group, an acyl halide group, an amide group, a carboxylic anhydride group, an alkyl halide group, an epoxide group, an aziridine group, an oxetane group, an azetidine group, a sulfonyl halide group, a chlorophosphate group, an α,β-unsaturated carbonyl group, an α,β-unsaturated nitrile group, a trifluoromethane-sulfonate group, a p-toluenesulfonate group, and an α,β-unsaturated methanesulfonyl group.

Suitable polyfunctional electrophiles include glutaric dialdehyde, succinic dialdehyde, and glyoxal; as well as compounds such as glyoxyl trimer and paraformaldehyde, bis(dimethyl) acetal, bis(diethyl) acetal, polymeric dialdehydes, such as oxidized starch. Other suitable polyfunctional electrophiles are a low molecular weight, difunctional aldehyde, such as glyoxal, 1,3-propane dialdehyde, 1,4-butane dialdehyde, 1,5-pentane dialdehyde, or 1,6-hexane.

Preferably, the polyfunctional electrophiles are polyfunctional isocyanates (i.e., polyisocyanates), each of which contains two or more isocyanate (—NCO) groups. These polyisocyanates can be aromatic, aliphatic, linear, branched, or cyclic. In some embodiments, the polyisocyanate contains, on average, 2 to 4 isocyanate groups. In particular embodiments, the polyisocyanate contains at least three isocyanate functional groups. In certain embodiments, the polyisocyanate is water insoluble.

In particular embodiments, the polyisocyanate used in this invention is an aromatic polyisocyanate. Desirably, the aromatic polyisocyanate includes a phenyl, tolyl, xylyl, naphthyl or diphenyl moiety as the aromatic component. In certain embodiments, the aromatic polyisocyanate is a polyisocyanurate of toluene diisocyanate, a trimethylol propane-adduct of toluene diisocyanate or a trimethylol propane-adduct of xylylene diisocyanate.

One class of suitable aromatic polyisocyanates are those having the generic structure shown below, and its structural isomers

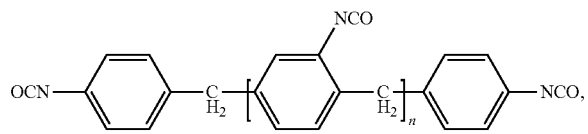

wherein n can vary from zero to a desired number (e.g., 0-50, 0-20, 0-10, and 0-6) depending on the type of polyamine or polyol used. Preferably, the number of n is limited to less than 6. The starting polyisocyanate may also be a mixture of polyisocyanates where the value of n can vary from 0 to 6. In the case where the starting polyisocyanate is a mixture of various polyisocyanates, the average value of n preferably falls in between 0.5 and 1.5. Commercially-available polyisocyanates include LUPRANATE® M20 (chemical name: polymeric methylene diphenyl diisocyanate, i.e., "PMDI"; commercially available from BASF containing isocyanate group "NCO" 31.5 wt %), where the average n is 0.7; PAPI™ 27 (PMDI commercially available from Dow Chemical having an average molecular weight of 340 and containing NCO 31.4 wt %) where the average n is 0.7; MONDUR® MR (PMDI containing NCO at 31 wt % or greater, commercially available from Covestro, Pittsburg, Pennsylvania) where the average n is 0.8; MONDUR® MR Light (PMDI containing NCO 31.8 wt %, commercially available from Covestro) where the average n is 0.8; MONDUR® 489 (PMDI commercially available from Covestro containing NCO 30-31.4 wt %) where the average n is 1; poly[(phenylisocyanate)-co-formaldehyde] (Aldrich Chemical, Milwaukee, WI), other isocyanate monomers such as DESMODUR® N3200 (poly(hexamethylene diisocyanate, commercially available from Covestro), and Takenate™ D-110N (trimethylol propane-adduct of xylylene diisocyanate, Mitsui Chemicals America, Inc., Rye Brook, NY, containing NCO 11.5 wt %), DESMODUR® L75 (a polyisocyanate base on toluene diisocyanate commercially available from Covestro), and DESMODUR® IL (another polyisocyanate based on toluene diisocyanate commercially available from Covestro).

The structures of certain commercially available polyisocyanates of the invention are shown below:

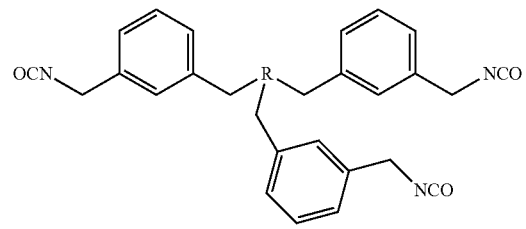

or its structural isomer. R can be a $C_1$-$C_{10}$ alkyl, $C_1$-$C_{10}$ ester, or an isocyanurate. Representative polyisocyanates of this structure are TAKENATE™ D-110N (Mitsui), DESMODUR® L75 (Covestro), and DESMODUR® IL (Covestro).

Polyisocyanate Takenate™ D-110N and other polyisocyanates are commercially available, typically in a ethyl acetate solution. Preferably, ethyl acetate is replaced with a solvent having a high flash point (e.g., at least 100° C., at least 120° C., and at least 150° C.). Suitable solvents include triacetin, triethyl citrate, ethylene glycol diacetate, benzyl benzoate, and combinations thereof.

As an illustration, Takenate™ D-110N (a trimethylol propane-adduct of xylylene diisocyanate solution in ethyl acetate) is combined with benzyl benzoate and vacuum distilled to remove ethyl acetate to obtain a polyisocyanate solution containing about 59% of the trimethylol propane-adduct of xylylene diisocyanate solution and 41% of benzyl benzoate. This polyisocyanate solution has a flash point of at least 60° C. This polyisocyanate solution in benzyl benzoate, together with PVP/PQ-11 or Flexan® II/CMC (carboxymethyl cellulose), can be used to prepare the microcapsule composition of this invention.

Other examples of the aromatic polyisocyanate include 1,5-naphthylene diisocyanate, 4,4'-diphenylmethane diisocyanate (MDI), hydrogenated MDI (HMDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), 4,4'-diisocyanatophenylperfluoroethane, phthalic acid bisisocyanatoethyl ester, also polyisocyanates with reactive halogen atoms, such as 1-chloromethylphenyl 2,4-diisocyanate, 1-bromomethyl-phenyl 2,6-diisocyanate, and 3,3-bis-chloromethyl ether 4,4'-diphenyldiisocyanate, and combinations thereof.

In other particular embodiments, the polyisocyanate is an aliphatic polyisocyanate such as a trimer of hexamethylene diisocyanate, a trimer of isophorone diisocyanate, and a biuret of hexamethylene diisocyanate. Exemplary aliphatic polyisocyanates include those commercially available, e.g., BAYHYDUR® N304 and BAYHYDUR® N305, which are aliphatic water-dispersible polyisocyanates based on hexamethylene diisocyanate; DESMODUR® N3600, DESMODUR® N3700, and DESMODUR® N3900, which are low viscosity, polyfunctional aliphatic polyisocyanates based on hexamethylene diisocyanate; and DESMODUR® 3600 and DESMODUR® N100 which are aliphatic polyisocyanates based on hexamethylene diisocyanate, each of which is available from Covestro, Pittsburgh, PA). More examples include 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, and combinations thereof. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane, dimer fatty acid diisocyanate, and combinations thereof.

The weight average molecular weight of certain polyisocyanates useful in this invention varies from 250 to 1000 Da and preferable from 275 to 500 Da.

The range of the polyfunctional electrophile (e.g., the polyisocyanate) content can vary from 0.2% to 40% (e.g., 0.4% to 35%, 0.5% to 30%, 1% to 25%, 2% to 25%, and 5% to 20%) by weight of the microcapsule. When the microcapsule is incorporated in a microcapsule composition, the amount of the polyisocyanate varies from 0.1% to 20%, preferably from 0.1% to 15%, more preferably from 0.2% to 10%, and even more preferably from 1.5% to 3.5%, all based on the total capsule composition.

In some embodiments, the polyfunctional isocyanate used in the preparation of the microcapsules of this invention is a single polyisocyanate. In other embodiments the polyisocyanate is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is used to prepare the polyurea/polyurethane polymers as capsule wall materials.

More examples of suitable polyisocyanates can be found in WO 2004/054362 and WO 2017/192648.

Polyphenols

The microcapsule composition of this invention optionally contains a polyphenol at a level of 0.01% to 10% (e.g., 0.05% to 8% and 0.1% to 5%) by weight of the composition.

Suitable polyphenols include those having a 3,4,5-trihydroxyphenyl group or 3,4-dihydroxypheny group. A preferred polyphenol is tannic acid, which has a typical chemical structure as follows:

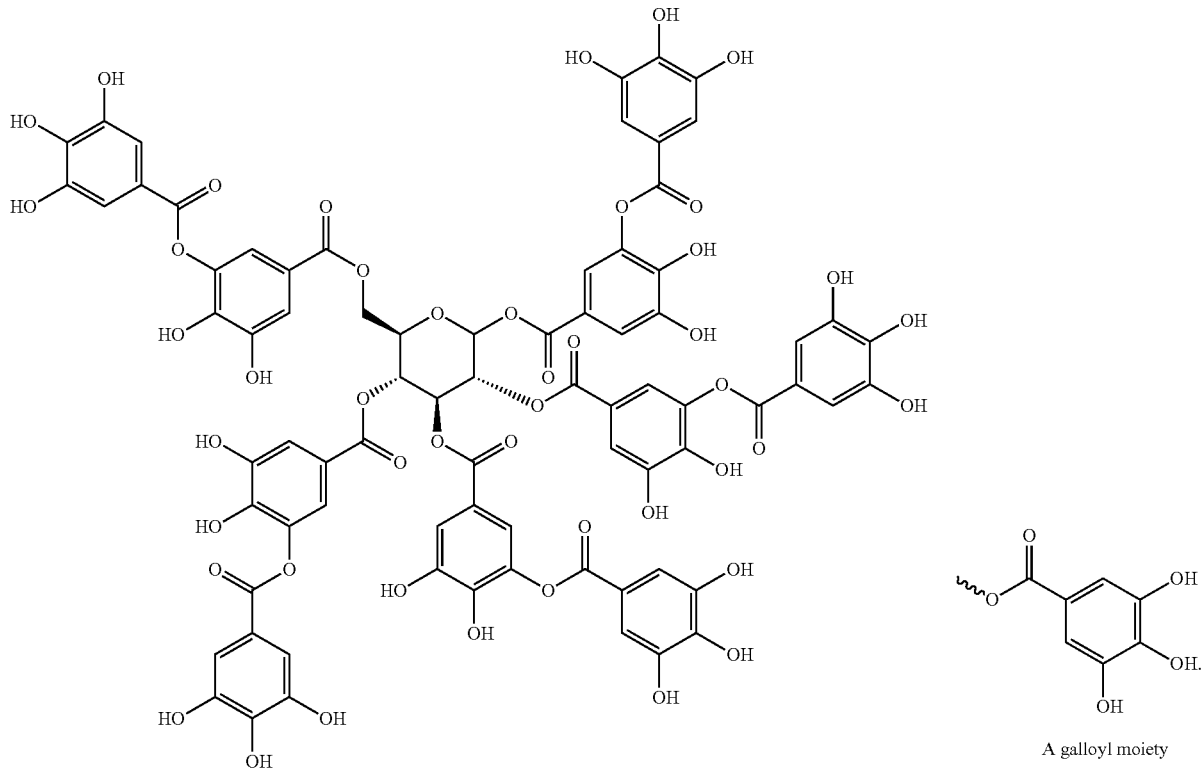

Representative structure of tannic acid

A galloyl moiety

The above chemical formula is often given as $C_{76}H_{52}O_{46}$, which corresponds with decagalloyl glucose. However, commercially available tannic acid typically comprises a mixture of polygalloyl glucoses or polygalloyl quinic acid esters with the number of galloyl moieties per molecule ranging from 2 up to 20 (e.g., 2 to 15 and 2 to 12) and a molecular weight of 400 Daltons to 3500 Daltons (e.g., 496 to 3232 Daltons, 496 Daltons to 2472 Daltons, 180+152n Daltons, and 192+152n Daltons, in which n is between 2 and 13). Tannic acid has a weak acidity (e.g., pKa around 6) with a pH value of 2 to 5 (e.g., 3-4 and 2.5 to 3.5) in an aqueous solution containing 1% of tannic acid. Tannic acid has a water solubility of 100 g/L to 2850 g/L (e.g., 250 g/L) at 25° C.

Tannic acid is usually extracted from any of the following plant parts: Tara pods (Caesalpinia spinosa), gallnuts from Rhus semialata or Quercus infectoria or Sicilian Sumac leaves (Rhus coriaria). Tannic acid is commercially available from suppliers such as Sigma-Aldrich (St Louis) and Ajinomoto OmniChem (Wetteren, Belgium) under the trademarks of Tanal® 01 (polygalloyl glucose, molecular weight 1440 Daltons), Tanal® 02 (polygalloyl glucose, molecular weight 1040 Daltons), and Tanal® 04 (polygalloyl quinic acid ester, molecular weight 860 Daltons).

In additional to polyphenols, other polyols can also be used. See polyols described in WO 2015/023961. Examples include pentaerythritol, dipentaerythritol, glycerol, polyglycerol, ethylene glycol, polyethylene glycol, trimethylolpropane, neopentyl glycol, sorbitol, erythritol, threitol, arabitol, xylitol, ribitol, mannitol, galactitol, fucitol, iditol, inositol, volemitol, isomalt, maltitol, lactitol, maltotriitol, maltotetraitol, polyglycitol, polyphenol, and combinations thereof.

Capsule Formation Aids

The microcapsule composition is typically prepared in the presence of a capsule formation aid, which can be a surfactant or dispersant. Capsule formation aids also improve the performance of the microcapsule composition. Performance is measured by the intensity of the fragrance released during certain stages, e.g., the pre-rub and post-rub phases in laundry applications. The pre-rub phase is the phase when the capsules have been deposited on the cloth, e.g., after a wash cycle using a capsule-containing fabric softener or detergent. The post-rub phase is after the capsules have been deposited and are broken by friction or other similar mechanisms.

In some embodiments, the capsule formation aid is a protective colloid or emulsifier including, e.g., maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide and ethylene oxide, polyvinylpyrrolidone (PVP), polyvinyl alcohols (PVA), sodium salt of naphthalene sulfonate condensate, carboxymethyl cellulose (CMC), fatty acid esters of polyoxyethylenated sorbitol, sodium dodecylsulfate, and combinations thereof. The concentration of the capsule formation aid (e.g., the surfactant and dispersant) varies from 0.1% to 5% (e.g., 0.2% to 4%, 0.5% to 4%, 0.5% to 2.5%, and 1% to 2%) by weight of the capsule composition.

Commercially available surfactants include, but are not limited to, sulfonated naphthalene-formaldehyde condensates such as MORWET® D-425 (sodium salt of alkylnaphthalenesulfonate formaldehyde condensate, commercially available from Akzo Nobel, Fort Worth, Texas); partially hydrolyzed polyvinyl alcohols such as MOWIOL®, e.g., MOWIOL® 3-83 (commercially available from Kuraray, Houston, Texas); ethylene oxide-propylene oxide block copolymers or poloxamers such as PLURONIC®, SYNPERONIC® or PLURACARE® materials (BASF); sulfonated polystyrenes such as FLEXAN® II (Akzo Nobel); ethylene-maleic anhydride polymers such as ZEMAC® (Vertellus Specialties Inc., Indianapolis, Indiana); and Polyquaternium series such as Polyquaternium 11 ("PQ11;" a copolymer of vinyl pyrrolidone and quaternized dimethylaminoethyl methacrylate; sold by BASF as LUVIQUAT® PQ11 AT 1).

Processing aids can also be used as capsule formation aids. They include hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly ((met)acrylic acid), poly(maleic acid), poly(alkyl(meth) acrylate-co-(meth)acrylic acid), poly(acrylic acid-co-maleic acid)copolymer, poly(alkyleneoxide), poly(vinyl-methylether), poly(vinylether-co-maleic anhydride), and the like, as well as poly-(ethyleneimine), poly((meth)acrylamide), poly (alkyleneoxide-co-dimethylsiloxane), poly(amino dimethylsiloxane), and the like, and their quaternized forms.

The capsule formation aid may also be used in combination with carboxymethyl cellulose ("CMC"), polyvinylpyrrolidone, polyvinyl alcohol, alkylnaphthalenesulfonate formaldehyde condensates, and/or a surfactant during processing to facilitate capsule formation. Examples of these surfactants include cetyl trimethyl ammonium chloride (CTAC), poloxamers such as PLURONIC® (e.g., PLURONIC® F127), PLURAFAC® (e.g., PLURAFAC® F127), or MIRANET®-N, saponins such as QNATURALE® (National Starch Food Innovation); or a gum Arabic such as Seyal or Senegal. In certain embodiments, the CMC polymer has a molecular weight (e.g., weight average molecular weight) range between 90,000 Daltons to 1,500,000 Daltons, preferably between 250,000 Daltons to 750,000 Daltons and more preferably between 400,000 Daltons to 750,000 Daltons. The CMC polymer has a degree of substitution between 0.1 to 3, preferably between 0.65 to 1.4, and more preferably between 0.8 to 1. The CMC polymer is present in the capsule slurry at a level from 0.1% to 2% and preferably from 0.3% to 0.7%. In other embodiments, polyvinylpyrrolidone used in this invention is a water-soluble polymer and has a molecular weight (e.g., weight average molecular weight) of 1,000 Daltons to 10,000,000 Daltons. Suitable polyvinylpyrrolidones are polyvinylpyrrolidones K12, K15, K17, K25, K30, K60, K90, or a mixture thereof. The amount of the polyvinylpyrrolidone is 2% to 50%, 5% to 30%, or 10% to 25% by weight of the microcapsule composition.

Catalysts

Sometimes, a catalyst is added to facilitate the formation of a capsule wall. Examples include metal carbonates, metal hydroxide, amino or organometallic compounds and include, for example, sodium carbonate, cesium carbonate, potassium carbonate, lithium hydroxide, 1,4-diazabicyclo

[2.2.2]octane (i.e., DABCO), N,N-dimethylaminoethanol, N,N-dimethylcyclohexylamine, bis-(2-dimethylaminoethyl) ether, N,N dimethylacetylamine, stannous octoate, and dibutyltin dilaurate.

Other Encapsulating Polymers

The microcapsule composition of this invention optionally has a second, third, fourth, fifth, or sixth microcapsule each formed of an encapsulating polymer selected from the group consisting of a sol-gel polymer (e.g., silica), polyacrylate, polyacrylamide, poly(acrylate-co-acrylamide), polyurea, polyurethane, starch, gelatin and gum Arabic, poly(melamine-formaldehyde), poly(urea-formaldehyde), and combinations thereof. A branched polyethyleneimine and its derivatives can also be coated onto the microcapsule wall to prepare a microcapsule having a positive zeta potential.

These encapsulating polymers are described in detail below.

Sol-gel Microcapsules. These microcapsules have a microcapsule wall formed of a sol-gel polymer, which is a reaction product of a sol-gel precursor via a polymerization reaction (e.g., hydrolyzation). Suitable sol-gel precursors are compounds capable of forming gels such as compounds containing silicon, boron, aluminum, titanium, zinc, zirconium, and vanadium. Preferred precursors are organosilicon, organoboron, and organoaluminum including metal alkoxides and b-diketonates.

Sol-gel precursors suitable for the purposes of the invention are selected in particular from the group of di-, tri- and/or tetrafunctional silicic acid, boric acid and alumoesters, more particularly alkoxysilanes (alkyl orthosilicates), and precursors thereof.

One example of sol-gel precursors suitable for the purposes of the invention are alkoxysilanes corresponding to the following general formula:

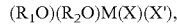

$(R_1O)(R_2O)M(X)(X')$, wherein X can be hydrogen or —$OR_3$; X' can be hydrogen or —$OR_4$; and $R_1$, $R_2$, $R_3$ and $R_4$ independently represent an organic group, more particularly a linear or branched alkyl group, preferably a $C_1$-$C_{12}$ alkyl. M can be Si, Ti, or Zr.

A preferred sol/gel precursor is alkoxysilanes corresponding to the following general formula: $(R_1O)(R_2O)Si(X)(X')$, wherein each of X, X', $R_1$, and $R_2$ are defined above.

Particularly preferred compounds are the silicic acid esters such as tetramethyl orthosilicate (TMOS) and tetraethyl orthosilicate (TEOS). A preferred compound includes Dynasylan® (organofunctional silanes commercially available from Degussa Corporation, Parsippany New Jersey, USA). Other sol-gel precursors suitable for the purposes of the invention are described, for example, in German Patent Application DE10021165. These sol-gel precursors are various hydrolyzable organosilanes such as, for example, alkylsilanes, alkoxysilanes, alkyl alkoxysilanes and organoalkoxysilanes. Besides the alkyl and alkoxy groups, other organic groups (for example allyl groups, aminoalkyl groups, hydroxyalkyl groups, etc.) may be attached as substituents to the silicon.

Recognizing that metal and semi metal alkoxide monomers (and their partially hydrolyzed and condensed polymers) such as tetramethoxy silane (TMOS), tetraethoxy silane (TEOS), etc. are very good solvents for numerous molecules and active ingredients is highly advantageous since it facilitates dissolving the active materials at a high concentration and thus a high loading in the final capsules.

Polyacrylate microcapsules, polyacrylamide microcapsules, and poly(acrylate-co-acrylamide) microcapsules. These microcapsules are prepared from corresponding precursors, which form the microcapsule wall. Preferred precursor are bi- or polyfunctional vinyl monomers including by way of illustration and not limitation, allyl methacrylate/acrylamide, triethylene glycol dimethacrylate/acrylamide, ethylene glycol dimethacrylate/acrylamide, diethylene glycol dimethacrylate/acrylamide, triethylene glycol dimethacrylate/acrylamide, tetraethylene glycol dimethacrylate/acrylamide, propylene glycol dimethacrylate/acrylamide, glycerol dimethacrylate/acrylamide, neopentyl glycol dimethacrylate/acrylamide, 1,10-decanediol dimethacrylate/acrylamide, pentaerythritol trimethacrylate/acrylamide, pentaerythritol tetramethacrylate/acrylamide, dipentaerythritol hexamethacrylate/acrylamide, triallyl-formal trimethacrylate/acrylamide, trimethylol propane trimethacrylate/acrylamide, tributanediol dimethacrylate/acrylamide, aliphatic or aromatic urethane diacrylates/acrylamides, difunctional urethane acrylates/acrylamides, ethoxylated aliphatic difunctional urethane methacrylates/acrylamides, aliphatic or aromatic urethane dimethacrylates/acrylamides, epoxy acrylates/acrylamides, epoxymethacrylates/acrylamides, 1,3-butylene glycol diacrylate/acrylamide, 1,4-butanediol dimethacrylate/acrylamide, 1,4-butaneidiol diacrylate/acrylamide, diethylene glycol diacrylate/acrylamide, 1,6-hexanediol diacrylate/acrylamide, 1,6-hexanediol dimethacrylate/acrylamide, neopentyl glycol diacrylate/acrylamide, polyethylene glycol diacrylate/acrylamide, tetraethylene glycol diacrylate/acrylamide, triethylene glycol diacrylate/acrylamide, 1,3-butylene glycol dimethacrylate/acrylamide, tripropylene glycol diacrylate/acrylamide, ethoxylated bisphenol diacrylate/acrylamide, ethoxylated bisphenol dimethylacrylate/acrylamide, dipropylene glycol diacrylate/acrylamide, alkoxylated hexanediol diacrylate/acrylamide, alkoxylated cyclohexane dimethanol diacrylate/acrylamide, propoxylated neopentyl glycol diacrylate/acrylamide, trimethylol-propane triacrylate/acrylamide, pentaerythritol triacrylate/acrylamide, ethoxylated trimethylolpropane triacrylate/acrylamide, propoxylated trimethylolpropane triacrylate/acrylamide, propoxylated glyceryl triacrylate/acrylamide, ditrimethyloipropane tetraacrylate/acrylamide, dipentaerythritol pentaacrylate/acrylamide, ethoxylated pentaerythritol tetraacrylate/acrylamide, PEG 200 dimethacrylate/acrylamide, PEG 400 dimethacrylate/acrylamide, PEG 600 dimethacrylate/acrylamide, 3-acryloyloxy glycol monoacrylate/acrylamide, triacryl formal, triallyl isocyanate, and triallyl isocyanurate.

The monomer is typically polymerized in the presence of an activation agent (e.g., an initiator) at a raised temperature (e.g., 30-90° C.) or under UV light. Exemplary initiators are 2,2'-azobis(isobutyronitrile) ("AIBN"), dicetyl peroxydicarbonate, di(4-tert-butylcyclohexyl)peroxydicarbonate, dioctanoyl peroxide, dibenzoyl peroxide, dilauroyl peroxide, didecanoyl peroxide, tert-butyl peracetate, tert-butyl perlaurate, tert-butyl perbenzoate, tert-butyl hydroperoxide, cumene hydroperoxide, cumene ethylperoxide, diisopropylhydroxy dicarboxylate, 2,2'-azobis(2,4-dimethylvaleronitrile), 1,1'-azobis-(cyclohexane-1-carbonitrile), dimethyl 2,2'-azobis(2-methylpropionate), 2,2'-azobis[2-methyl-N-(2-hydroxyethyl)propionamide, sodium persulfate, benzoyl peroxide, and combinations thereof.

Emulsifiers used in the formation of polyacrylate/polyacrylamide/poly(acrylate-co-acrylamide) capsule walls are typically anionic emulsifiers including by way of illustration and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates. The amount of anionic emulsifier is anywhere from 0.1 to 40 percent by weight of all constituents, more preferably from 0.5 to 10 percent, more preferably 0.5 to 5 percent by weigh.

Aminoplasts and Gelatin. A representative process used for aminoplast encapsulation is disclosed in U.S. Pat. No. 3,516,941 and US 2007/0078071, though it is recognized that many variations with regard to materials and process steps are possible. Another encapsulation process, i.e., gelatin encapsulation, is disclosed in U.S. Pat. No. 2,800,457. Both processes are discussed in the context of fragrance encapsulation for use in consumer products in U.S. Pat. Nos. 4,145,184 and 5,112,688 respectively. Polymer systems are well-known in the art and non-limiting examples of these include aminoplast capsules and encapsulated particles as disclosed in GB 2006709 A; the production of microcapsules having walls comprising styrene-maleic anhydride reacted with melamine-formaldehyde precondensates as disclosed in U.S. Pat. No. 4,396,670; an acrylic acid-acrylamide copolymer, cross-linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amido-aldehyde resin in-situ polymerized capsules disclosed in EP 0 158 449 A1; etherified urea-formaldehyde polymer as disclosed in U.S. Pat. No. 5,204,185; melamine-formaldehyde microcapsules as described in U.S. Pat. No. 4,525,520; cross-linked oil-soluble melamine-formaldehyde precondensate as described in U.S. Pat. No. 5,011,634; capsule wall material formed from a complex of cationic and anionic melamine-formaldehyde precondensates that are then cross-linked as disclosed in U.S. Pat. No. 5,013,473; polymeric shells made from addition polymers such as condensation polymers, phenolic aldehydes, urea aldehydes or acrylic polymer as disclosed in U.S. Pat. No. 3,516,941; urea-formaldehyde capsules as disclosed in EP 0 443 428 A2; melamine-formaldehyde chemistry as disclosed in GB 2 062 570 A; and capsules composed of polymer or copolymer of styrene sulfonic acid in acid of salt form, and capsules cross-linked with melamine-formaldehyde as disclosed in U.S. Pat. No. 4,001,140.

Urea-formaldehyde and melamine formaldehyde Capsules. Urea-formaldehyde and melamine-formaldehyde pre-condensate capsule shell wall precursors are prepared by means of reacting urea or melamine with formaldehyde where the mole ratio of melamine or urea to formaldehyde is in the range of from 10:1 to 1:6, preferably from 1:2 to 1:5. For purposes of practicing this invention, the resulting material has a molecular weight in the range of from 156 to 3000. The resulting material may be used 'as-is' as a cross-linking agent for the aforementioned substituted or un-substituted acrylic acid polymer or copolymer or it may be further reacted with a $C_1$-$C_6$ alkanol, e.g., methanol, ethanol, 2-propanol, 3-propanol, 1-butanol, 1-pentanol or 1-hexanol, thereby forming a partial ether where the mole ratio of melamine/urea:formaldehyde:alkanol is in the range of 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. No. 6,261,483, and Lee et al. (2002) *J. Microencapsulation* 19, 559-569.

Examples of urea-formaldehyde pre-condensates useful in the practice of this invention are URAC™ 180 and URAC™ 186, trademarks of Cytec Technology Corp. of Wilmington, DE. Examples of melamine-formaldehyde pre-condensates useful in the practice if this invention, include, but are not limited to, CYMEL® U-60, CYMEL® U-64 and CYMEL® U-65, trademarks of Cytec Technology Corp. of Wilmington, DE. It is preferable to use, as the precondensate for cross-linking, the substituted or un-substituted acrylic acid polymer or co-polymer. In practicing this invention, the range of mole ratios of urea-formaldehyde precondensate/melamine-formaldehyde pre-condensate to substituted/un-substituted acrylic acid polymer/co-polymer is in the range of from 9:1 to 1:9, preferably from 5:1 to 1:5 and most preferably from 2:1 to 1:2.

In one embodiment of the invention, microcapsules with polymer(s) composed of primary and/or secondary amine reactive groups or mixtures thereof and cross-linkers can also be used. See US 2006/0248665. The amine polymers can possess primary and/or secondary amine functionalities and can be of either natural or synthetic origin. Amine-containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the LUPAMIN® series of polyvinyl formamides available from BASF. The molecular weights of these materials can range from 10,000 to 1,000,000.

Urea-formaldehyde or melamine-formaldehyde capsules can also include formaldehyde scavengers, which are capable of binding free formaldehyde. When the capsules are for use in aqueous media, formaldehyde scavengers such as sodium sulfite, melamine, glycine, and carbohydrazine are suitable. When the capsules are aimed to be used in products having low pH, e.g., fabric care conditioners, formaldehyde scavengers are preferably selected from beta diketones, such as beta-ketoesters, or from 1,3-diols, such as propylene glycol. Preferred beta-ketoesters include alkylmalonates, alkyl aceto acetates and polyvinyl alcohol aceto acetates.

The microcapsule composition of this invention optionally contains one or more additional microcapsules, e.g., a second, third, fourth, fifth, or sixth microcapsules. Each of these microcapsules can be any of the microcapsule described above.

These additional microcapsules can be any of the microcapsules described above but different from each other in term of the microcapsule size, the degree of polymerization, the degree of crosslinking, the encapsulating polymer, the thickness of the wall, the active material, the ratio between the wall material and the active material, the rupture force or fracture strength, and the like.

Active Materials

The core of the capsules of the invention can include one or more active materials including, but not limited to, flavors and/or fragrance ingredients such as fragrance oils. Individual active materials that can be encapsulated include those listed in WO 2016049456, pages 38-50. These active material include flavor or fragrance ingredients, taste masking agents, taste sensates, malodor counteracting agents, vitamins or derivatives thereof, antibacterials, sunscreen actives, antioxidants, anti-inflammatory agents, fungicide, anesthetics, analgesics, antifungal agents, antibiotics, antiviral agents, anti-parasitic agents, anti-infectious, anti-acne agents, dermatological active ingredients, enzymes and co-enzymes, skin whitening agents, anti-histamines, chemotherapeutic agents, insect repellents, emollient, skin moisturizing agent, wrinkle control agent, UV protection agent, fabric softener active, hard surface cleaning active, skin or hair conditioning agent, animal repellent, vermin repellent, flame retardant, antistatic agent, nanometer to micron size inorganic solid, polymeric or elastomeric particle, and combination thereof.

In addition to the active materials listed above, the products of this invention can also contain, for example, the following dyes, colorants or pigments: lactoflavin (riboflavin), beta-carotene, riboflavin-5'-phosphate, alpha-carotene, gamma-carotene, cantaxanthin, erythrosine, curcumin, quinoline yellow, yellow orange S, tartrazine, bixin, norbixin (annatto, orlean), capsanthin, capsorubin, lycopene, beta-apo-8'-carotenal, beta-apo-8'-carotenic acid ethyl ester, xantophylls (flavoxanthin, lutein, cryptoxanthin, rubixanthin, violaxanthin, rodoxanthin), fast carmine (carminic acid, cochineal), azorubin, cochineal red A (Ponceau 4 R), beetroot red, betanin, anthocyanins, amaranth, patent blue V, indigotine I (indigo-carmine), chlorophylls, copper compounds of chlorophylls, acid brilliant green BS (lissamine green), brilliant black BN, vegetable carbon, titanium dioxide, iron oxides and hydroxides, calcium carbonate, aluminum, silver, gold, pigment rubine BK (lithol rubine BK), methyl violet B, victoria blue R, victoria blue B, acilan brilliant blue FFR (brilliant wool blue FFR), naphthol green B, acilan fast green 10 G (alkali fast green 10 G), ceres yellow GRN, sudan blue II, ultramarine, phthalocyanine blue, phthalocayanine green, fast acid violet R. Further naturally obtained extracts (for example paprika extract, black carrot extract, red cabbage extract) can be used for coloring purposes. Goods results are also achieved with the colors named in the following, the so-called aluminum lakes: FD & C Yellow 5 Lake, FD & C Blue 2 Lake, FD & C Blue 1 Lake, Tartrazine Lake, Quinoline Yellow Lake, FD & C Yellow 6 Lake, FD & C Red 40 Lake, Sunset Yellow Lake, Carmoisine Lake, Amaranth Lake, Ponceau 4R Lake, Erythrosyne Lake, Red 2G Lake, Allura Red Lake, Patent Blue V Lake, Indigo Carmine Lake, Brilliant Blue Lake, Brown HT Lake, Black PN Lake, Green S Lake and mixtures thereof.

When the active material is a fragrance, it is preferred that fragrance ingredients within a fragrance having a ClogP of 0.5 to 15 are employed. For instance, the ingredients having a ClogP value between 0.5 to 8 (e.g., between 1 to 12, between 1.5 to 8, between 2 and 7, between 1 and 6, between 2 and 6, between 2 and 5, between 3 and 7) are 25% or greater (e.g., 50% or greater and 90% or greater) by the weight of the fragrance.

It is preferred that a fragrance having a weight-averaged ClogP of 2.5 and greater (e.g., 3 or greater, 2.5 to 7, and 2.5 to 5) is employed. The weight-averaged ClogP is calculated as follows:

$$C \log P = \{\text{Sum}[(Wi)(\text{ClogP})i]\}/\{\text{Sum } Wi\},$$

in which $Wi$ is the weight fraction of each fragrance ingredient and $(\text{ClogP})i$ is the ClogP of that fragrance ingredient.

As an illustration, it is preferred that greater than 60 wt % (preferably greater than 80 wt % and more preferably greater than 90 wt %) of the fragrance chemicals have ClogP values of greater than 2 (preferably greater than 3.3, more preferably greater than 4, and even more preferably greater than 4.5).

Those with skill in the art will appreciate that many fragrances can be created employing various solvents and fragrance chemicals. The use of a relatively low to intermediate ClogP fragrance ingredients will result in fragrances that are suitable for encapsulation. These fragrances are generally water-insoluble, to be delivered through the capsule systems of this invention onto consumer products in different stages such as damp and dry fabric. Without encapsulation, the free fragrances would normally have evaporated or dissolved in water during use, e.g., wash. Though high ClogP materials are generally well delivered from a regular (non-encapsulated) fragrance in a consumer product, they have excellent encapsulation properties and are also suitable for encapsulation for overall fragrance character purposes, very long-lasting fragrance delivery, or overcoming incompatibility with the consumer product, e.g., fragrance materials that would otherwise be instable, cause thickening or discoloration of the product or otherwise negatively affect desired consumer product properties.

High performing, high impact fragrances are envisaged. One class of high performing fragrances is described in WO 2018/071897. These fragrances have a high intensity accord containing (i) at least 7 wt % (e.g., 7 to 95 wt %) of Class 1 fragrance ingredients, (ii) 5 to 95 wt % (e.g., 5 to 80 wt %, 10 to 80 wt %, and 10 to 70 wt %) of Class 2 fragrance ingredients, and (iii) 0 to 80 wt % of Class 3 fragrance ingredients, in which the Class 1 fragrance ingredients each have an experimental velocity of 8.5 cm/second or greater, the Class 2 fragrance ingredients each have an experimental velocity of less than 8.5 cm/second and greater than 5 cm/second, and the Class 3 fragrance ingredients each have an experimental velocity of 5 cm/second or less. In some embodiments, the sum of the Class 1 fragrance ingredients, the Class 2 fragrance ingredients, and the Class 3 fragrance ingredients is 100%. In other embodiments, the sum of Class 1 and Class 2 ingredients is 20% to 100 wt %. Other high impact fragrances suitable for use in this invention are those described in WO 1999/065458, U.S. Pat. No. 9,222,055, US 2005/0003975, and WO1997/034987.

In some embodiments, the amount of encapsulated active material is from 5% to 95% (e.g., 10% to 90%, 15% to 80%, and 20% to 60%) by weight of the microcapsule composition. The amount of the capsule wall is from 0.5% to 30% (e.g., 1% to 25%, 2 to 20% and 5 to 15%) also by weight of the microcapsule composition. In other embodiments, the amount of the encapsulated active material is from 15% to 99.5% (e.g., 20% to 98% and 30% to 90%) by weight of the microcapsule, and the amount of the capsule wall is from 0.5% to 85% (e.g., 2 to 50% and 5 to 40%) by weight of the microcapsule.

Adjunct Materials

In addition to the active materials, the present invention also contemplates the incorporation of adjunct materials including solvent, emollients, and core modifier materials in the core encapsulated by the capsule wall. Other adjunct materials are solubility modifiers, density modifiers, stabilizers, viscosity modifiers, pH modifiers, or any combination thereof. These modifiers can be present in the wall or core of the capsules, or outside the capsules in delivery system. Preferably, they are in the core as a core modifier.

The one or more adjunct material may be added in the amount of 0.01% to 40% (e.g., 0.5% to 30%) by weight of the microcapsule. Suitable examples include those described in WO 2016/049456, pages 55-57 and US 2016/0158121, pages 15-18.

Deposition Aids

An exemplary deposition aid useful in the microcapsule composition of this invention is a copolymer of acrylamide and acrylamidopropyltrimonium chloride. This copolymer facilitates the deposition of the microcapsule onto a hard surface (e.g., hair, skin, fiber, furniture, and floor). The copolymer generally has an average molecular weight (e.g., weight average molecular mass (Mw) determined by size exclusion chromatography) of 2,000 Daltons to 10,000,000 Daltons with a lower limit of 2,000, 5,000, 10,000, 20,000, 50,000, 100,000, 250,000, 500,000, or 800,000 Daltons and an upper limit of 10,000,000, 5,000,000, 2,000,000, 1,000,000, or 500,000 Daltons (e.g., 500,000 to 2,000,000 and 800,000 to 1,500,000 Daltons). The charge density of the copolymer ranges from 1 meq/g to 2.5 meq/g, preferably from 1.5 to 2.2 meq/g. The copolymer of acrylamide and acrylamidopropyltrimonium chloride is commercially available from various vendors such as Ashland as N-Hance™ SP-100 and Ciba SALCARE® SC60.

Other suitable deposition aids include anionically, cationically, nonionically, or amphoteric water-soluble polymers. Suitable deposition aids include chitosan, polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-37, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, a methacrylamidopropyltrimonium chloride/acrylamide copolymer, copolymer of acrylamide and acrylamidopropyltrimonium chloride, 3-acrylamidopropyl trimethylammonium polymer or its copolymer, diallyldimethylammoniumchloride polymer and its copolymer, a polysaccharide with saccharide unit functionalized with hydroxypropyl trimmonium, and combinations thereof. More examples of the deposition aid are described in WO 2016049456, pages 13-27; US 2013/0330292; US 2013/0337023; and US 2014/0017278.

Additional depositional aids are those cationic polymers described in WO2016032993. These cationic polymers are typically characterized by a relatively high charge density (e.g., from 4 meq/g, or from 5 meq/g, or from 5.2 meq/g to 12 meq/g, or to 10 meq/g, or to 8 meq/g or to 7 meq/g, or to 6.5 meq/g. The cationic polymers are comprised of structural units that are nonionic, cationic, anionic, or mixtures thereof. In some aspects, the cationic polymer comprises from 5 mol % to 60 mol %, or from 15 mol % to 30 mol %, of a nonionic structural unit derived from a monomer selected from the group consisting of (meth)acrylamide, vinyl formamide, N,N-dialkyl acrylamide, N,N-dialkylmethacrylamide, $C_1$-$C_{12}$ alkyl acrylate, $C_1$-$C_{12}$ hydroxyalkyl acrylate, polyalkylene glyol acrylate, $C_1$-$C_{12}$ alkyl methacrylate, $C_1$-$C_{12}$ hydroxyalkyl methacrylate, polyalkylene glycol methacrylate, vinyl acetate, vinyl alcohol, vinyl formamide, vinyl acetamide, vinyl alkyl ether, vinyl pyridine, vinyl pyrrolidone, vinyl imidazole, vinyl caprolactam, and mixtures thereof.

In some aspects, the cationic polymer comprises a cationic structural unit at the level of 30 mol % to 100 mol %, or 50 mol % to 100 mol %, or 55 mol % to 95 mol %, or 70 mol % to 85 mol % by mass of the cationic polymer. The cationic structural unit is typically derived from a cationic monomer such as N,N-dialkylaminoalkyl methacrylate, N,N-dialkylaminoalkyl acrylate, N,N-dialkylaminoalkyl acrylamide, N,N-dialkylaminoalkylmethacrylamide, methacylamidoalkyl trialkylammonium salts, acrylamidoalkylltrialkylamminium salts, vinylamine, vinylimine, vinyl imidazole, quaternized vinyl imidazole, diallyl dialkyl ammonium salts, and mixtures thereof. Preferably, the cationic monomer is selected from the group consisting of diallyl dimethyl ammonium salts (DADMAS), N,N-dimethyl aminoethyl acrylate, N,N-dimethyl aminoethyl methacrylate (DMAM), [2-(methacryloylamino)ethyl]tri-methylammonium salts, N,N-dimethylaminopropyl acrylamide (DMAPA), N,N-dimethylaminopropyl methacrylamide (DMAPMA), acrylamidopropyl trimethyl ammonium salts (APTAS), methacrylamidopropyl trimethylammonium salts (MAPTAS), quaternized vinylimidazole (QVi), and mixtures thereof.

In some aspects, the cationic polymer comprises an anionic structural unit at a level of 0.01 mol % to 15 mol %, 0.05 mol % to 10 mol %, 0.1 mol % to 5 mol %, or 1% to 4% of by mass of the cationic polymer. In some aspects, the anionic structural unit is derived from an anionic monomer selected from the group consisting of acrylic acid (AA), methacrylic acid, maleic acid, vinyl sulfonic acid, styrene sulfonic acid, acrylamidopropylmethane sulfonic acid (AMPS) and their salts, and mixtures thereof.

Exemplary cationic polymers include polyacrylamide-co-DADMAS, polyacrylamide-co-DADMAS-co-acrylic acid, polyacrylamide-co-APTAS, polyacrylamide-co-MAPTAS, polyacrylamide-co-QVi, polyvinyl formamide-co-DADMAS, poly(DADMAS), polyacrylamide-co-MAPTAS-coacrylic acid, polyacrylamide-co-APTAS-co-acrylic acid, and mixtures thereof.

The deposition aid is generally present at a level of 0.01% to 50% (with a lower limit of 0.01%, 0.05%, 0.1%, 0.5%, 1%, 2%, or 5% and an upper limit of 50%, 40%, 30%, 20%, 15%, or 10%, e.g., 0.1% to 30%, 1% to 20%, 2% to 15%, and 5% to 10%) by weight of the microcapsule composition. In a consumer product such as a shampoo, the deposition aid is generally present at a level of 0.001% to 20% (with a lower limit of 0.001%, 0.005%, 0.01%, 0.02%, or 0.05% and an upper limit of 20%, 15%, 10%, 5%, 2%, or 1%, e.g., 0.005% to 10%, 0.01% to 5%, and 0.02% to 0.5%) by weight of the shampoo composition. The capsule deposition aid can be added during the preparation of the microcapsules or it can be added after the microcapsules have been made.

A second capsule deposition aid from 0.01% to 25%, more preferably from 5% to 20% can be added to the microcapsule composition. The second capsule formation deposition aid can be selected from the above-described deposition aid.

Additional Components

The microcapsule composition of this invention can include one or more non-confined or unencapsulated active materials from 0.01 to 50%, more preferably from 5 to 40%.

The capsule delivery system can also contain one or more other delivery system such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof. More exemplary delivery systems that can be incorporated are coacervate capsules, cyclodextrin delivery systems, and pro-perfumes.

Examples of additional components include those described in US 2016/0158121.

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethylammonium ion). A precursor can be ester and another suitable derivative, which, during the process of preparing a polyurea or polyurethane capsule composition of this invention, is capable of converting to the compound, polymer, or agent and being used in preparing the polyurea or polyurethane capsule composition. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine.

Certain compounds, polymers, and agents have one or more stereocenters, each of which can be in the R configuration, the S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, and etc. Guanidine includes guanidine hydrochloride, guanidine carbonate, guanidine thiocyanate, and other guanidine salts including their hydrates. Ornithine includes L-ornithine and its salts/hydrates (e.g., monohydrochloride) and D-ornithine and its salts/hydrates (e.g., monohydrochloride).

The microcapsule composition of this invention can be a slurry containing in a solvent (e.g., water) the capsule at a level 0.1 to 80% (preferably 1 to 65% and more preferably 5 to 45%) by weight of the capsule delivery system. An exemplary microcapsule composition of this invention contains a plurality of microcapsules each dispersed in an aqueous phase and is stable for at least 7 days (e.g., at least 10 days, at least 30 days, and at least 60 days) at 40° C. Stability is measured (e.g., in a graduated cylinder) by the separation of a clear aqueous phase from the microcapsule composition. The microcapsule composition is deemed stable if, by volume of the microcapsule composition, less than 10% of a clear aqueous phase is separated. The microcapsule composition is considered stable when (i) the composition has a viscosity of 3000 cP or less (e.g., 2000 cP or less) and (ii) 20% or less (e.g., 15% or less, and 10% or less) water by volume of the composition is separated from the composition. The volume of the separated water can be readily measured by a convention method, e.g., a graduated cylinder.

Microcapsule compositions are known to have the tendency to form into gels, unsuitable for use in many consumer products. The viscosity of the gelled-out composition increases to at least 3000 centipoise (cP) (e.g., at least 6000 cP). The viscosity can be readily measured on rheometer, for example a RheoStress™ 1 instrument (Commercially available from ThermoScientific), using rotating disks at a shear rate of 21 $s^{-1}$ and a temperature of 25° C.

In some embodiments, the microcapsule composition is purified by washing the capsule slurry with water until a neutral pH (pH of 6 to 8) is achieved. For the purposes of the present invention, the capsule suspension can be washed using any conventional method including the use of a separatory funnel, filter paper, centrifugation and the like. The capsule suspension can be washed one, two, three, four, five, six, or more times until a neutral pH, e.g., pH 6-8 and 6.5-7.5, is achieved. The pH of the purified capsules can be determined using any conventional method including, but not limited to pH paper, pH indicators, or a pH meter.

A capsule composition is "purified" in that it is 80%, 90%, 95%, 97%, 98% or 99% homogeneous to capsules. In accordance with the present invention, purity is achieved by washing the capsules until a neutral pH is achieved, which is indicative of removal of unwanted impurities and/or starting materials, e.g., polyisocyanate, cross-linking agent and the like.

In certain embodiments of this invention, the purification of the capsules includes the additional step of adding a salt to the capsule suspension prior to the step of washing the capsule suspension with water. Exemplary salts of use in this step of the invention include, but are not limited to, sodium chloride, potassium chloride or bi-sulphite salts. See US 2014/0017287.

The microcapsule composition of this invention can also be dried, e.g., spray dried, heat dried, and belt dried, to a solid form. In a spray drying process, a spray dry carrier is added to a microcapsule composition to assist the removal of water from the slurry. See US20120151790, US20140377446, US20150267964, US20150284189, and US20160097591.

According to one embodiment, the spray dry carriers can be selected from the group consisting of carbohydrates such as chemically modified starches and/or hydrolyzed starches, gums such as gum Arabic, proteins such as whey protein, cellulose derivatives, clays, synthetic water-soluble polymers and/or copolymers such as polyvinyl pyrrolidone, polyvinyl alcohol. The spray dry carriers may be present in an amount from 1 to 50%, more preferably from 5 to 20%, by weight of the microcapsule composition in slurry.

Optionally, a free flow agent (anticaking agent) of silicas which may be hydrophobic (i.e. silanol surface treated with halogen silanes, alkoxysilanes, silazanes, siloxanes, etc. such as Sipernat® D17, Aerosil® R972 and R974 (available from Degussa), etc.) and/or hydrophilic such as Aerosil® 200, Sipernat® 22S, Sipernat® 50S, (available from Degussa), Syloid® 244 (available from Grace Davison), may be present from 0.01 to 10%, more preferable from 0.5 to 5%, by weight of the microcapsule composition in slurry.

Humectants and viscosity control/suspending agents can also be added to facilitate spray drying. These agents are disclosed in U.S. Pat. Nos. 4,446,032 and 6,930,078. Details of hydrophobic silica as a functional delivery vehicle of active materials other than a free flow/anticaking agent are disclosed in U.S. Pat. Nos. 5,500,223 and 6,608,017.

The spray drying inlet temperature is in the range of 150 to 240° C., preferably between 170 and 230° C., more preferably between 190 and 220° C.

As described herein, the spray-dried microcapsule composition is well suited for use in a variety of all dry (anhydrous) products: powder laundry detergent, fabric softener dryer sheets, household cleaning dry wipes, powder dish detergent, floor cleaning cloths, or any dry form of personal care products (e.g. shampoo powder, deodorant powder, foot powder, soap powder, baby powder), etc. Because of high fragrance and/or active agent concentration in the spray-dried products of the present invention, characteristics of the aforementioned consumer dry products will not be adversely affected by a small dosage of the spray-dried products.

The microcapsule composition can also be sprayed as a slurry onto a consumer product, e.g., a fabric care product. By way of illustration, a liquid delivery system containing capsules is sprayed onto a detergent powder during blending to make granules. See US 2011/0190191. In order to increase fragrance load, water-absorbing material, such as zeolite, can be added to the delivery system.

Alternatively, granulates in a consumer product are prepared in a mechanical granulator in the presence of a granulation auxiliary such as non-acid water-soluble organic crystalline solids. See WO 2005/097962.

Zeta Potentials and Rupture Forces

The microcapsule of this invention is positively charged as indicated by a zeta potential of at least 10 mV, preferably at least 25 mV (e.g., 25 to 200 mV), and more preferably at least 40 mV (e.g., 40 to 100 mV).

Zeta potential is a measurement of electrokinetic potential in the microcapsule. From a theoretical viewpoint, zeta potential is the potential difference between the water phase (i.e., the dispersion medium) and the stationary layer of water attached to the surface of the microcapsule.

The zeta potential is an important indicator of the stability of the microcapsule in compositions or consumer products. Typically, a microcapsule having a zeta potential of 10 to 25 mV shows a moderate stability. Similarly, a microcapsule having a zeta potential of 25 to 40 mV shows a good stability and a microcapsule having a zeta potential of 40 to 100 mV shows excellent stability. Not to be bound by any theory, the microcapsule of this invention has a desirable zeta potential making it suitable for use in consumer products with improved stability.

The zeta potential can be calculated using theoretical models and an experimentally-determined electrophoretic mobility or dynamic electrophoretic mobility. The zeta potential is conventionally measured by methods such as microelectrophoresis, or electrophoretic light scattering, or electroacoustic phenomena. For more detailed discussion on measurement of zeta potential, see Dukhin and Goetz, "Ultrasound for characterizing colloids", Elsevier, 2002.

The microcapsule of this invention has a fracture strength of 0.2 to 80 MPa (e.g., 0.5 to 60 MPa, 1 to 50 MPa, and 5 to 30 MPa). The fracture strength of each microcapsule is calculated by dividing the rupture force (in Newtons) by the cross-sectional area of the respective microcapsule ($\pi r^2$, where r is the radius of the particle before compression). The measurement of the rupture force and the cross-sectional area is performed following the methods described in Zhang et al., *J. Microencapsulation* 18(5), 593-602 (2001).

The microcapsule of this invention has a rupture force of less than 10 millinewtons ("mN") such as 0.1 mN to 10 mN, 0.2 mN to 8 mN, 0.3 mN to 5 mN, 0.1 mN to 2 mN, 0.1 mN, 0.5 mN, 1 mN, 2 mN, 5 mN, and 8 mN. The rupture force is the force needed to rupture the microcapsules. Its measurement is based on a technique known in the art as micro-manipulation. See Zhang et al., *Journal of Microencapsulation* 16(1), 117-124 (1999).

Applications.

The microcapsule of the present invention is well-suited for use, without limitation, in the following additional products:

A) Household products
  i. Liquid or Powder Laundry Detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818
  ii. Unit Dose Pouches, Tablets and Capsules such as those described in EP 1 431 382 A1, US 2013/0219996 A1, US 2013/0284637 A1, and U.S. Pat. No. 6,492,315. These unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%). They can contain no water to limit the water content as low as less than 30% (e.g., less than 20%, less than 10%, and less than 5%).
  iii. Scent Boosters such as those described in U.S. Pat. Nos. 7,867,968, 7,871,976, 8,333,289, US 2007/0269651 A1, and US2014/0107010 A1.
  iv. Fabric Care Products such as Rinse Conditioners (containing 1-30 weight % of a fabric conditioning active), Fabric Liquid Conditioners (containing 1 to 30 weight % of a fabric conditioning active), Tumble Drier Sheets, Fabric Refreshers, Fabric Refresher Sprays, Ironing Liquids, and Fabric Softener Systems such as those described in U.S. Pat. Nos. 6,335,315, 5,674,832, 5,759,990, 5,877,145, 5,574,179, 5,562,849, 5,545,350, 5,545,340, 5,411,671, 5,403,499, 5,288,417, 4,767,547 and 4,424,134
     Liquid fabric softeners/fresheners contain at least one fabric softening agent present, preferably at a concentration of 1 to 30% (e.g., 4 to 20%, 4 to 10%, and 8 to 15%). The ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01 to 2.5%, preferably 0.02 to 1.25% and more preferably 0.1 to 0.63%. As another example, when the fabric softening agent is 20% by weight of the fabric softener, the active material is 0.04 to 10%, preferably 0.08 to 5% and more preferably 0.4 to 2.5%. The active material is a fragrance, malodor counteractant or mixture thereof. The liquid fabric softener can have 0.15 to 15% of capsules (e.g., 0.5 to 10%, 0.7 to 5%, and 1 to 3%). When including capsules at these levels, the neat oil equivalent (NOE) in the softener is 0.05 to 5% (e.g., 0.15 to 3.2%, 0.25 to 2%, and 0.3 to 1%).

Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as Rewoquat® WE 18 commercially available from Evonik Industries and Stepantex® SP-90 commercially available from Stepan Company.

v. Liquid dish detergents such as those described in U.S. Pat. Nos. 6,069,122 and 5,990,065 vi. Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562 vii. All-purpose Cleaners including bucket dilutable cleaners and toilet cleaners viii. Bathroom Cleaners ix. Bath Tissue x. Rug Deodorizers xi. Candles xii. Room Deodorizers xiii. Floor Cleaners xiv. Disinfectants xv. Window Cleaners xvi. Garbage bags/trash can liners xvii. Air Fresheners including room deodorizer and car deodorizer, scented candles, sprays, scented oil air freshener, Automatic spray air freshener, and neutralizing gel beads xviii. Moisture absorber xix. Household Devices such as paper towels and disposable Wipes xx. Moth balls/traps/cakes xxi. liquid fragrance compositions each comprising: (i) 3 wt % to 40 wt % (e.g., 5 wt % to 35 wt %, preferably 8 wt % to 30 wt %, and more preferably 10 wt % to 3 wt %) of a fragrance in the form of neat oil or encapsulated in a microcapsule, (ii) 0.5 wt % to 5 wt % (preferably 0.2 wt % to 3 wt %, and more preferably 0.5 wt % to 2.5 wt %) of glyceryl ricinoleate, and (iii) 60 wt % to 95 wt % of water. All amounts are based on the weight of the liquid fragrance composition.

b) Baby Care Products
  i. Diaper Rash Cream/Balm
  ii. Baby Powder c) Baby Care Devices
  i. Diapers
  ii. Bibs
  iii. Wipes d) Oral Care Products. Tooth care products (as an example of preparations according to the invention used for oral care) generally include an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or Laponite®, sweeteners, for example saccharin, taste correctors for unpleasant taste sensations, taste correctors for further, normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol derivatives, (for example L-menthyllactate, L-menthylalkylcarbonates, menthone ketals, menthane carboxylic acid amides), 2,2,2-trialkylacetic acid amides (for example 2,2-diisopropylpropionic acid methyl amide), icilin and icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors.

i. Tooth Paste. An exemplary formulation as follows:
    1. calcium phosphate 40-55%
    2. carboxymethyl cellulose 0.8-1.2%
    3. sodium lauryl sulfate 1.5-2.5%
    4. glycerol 20-30%
    5. saccharin 0.1-0.3%
    6. flavor oil 1-2.5%
    7. water q.s. to 100%
      A typical procedure for preparing the formulation includes the steps of (i) mixing by a blender according to the foregoing formulation to provide a toothpaste, and (ii) adding a composition of this invention and blending the resultant mixture till homogeneous.
  ii. Tooth Powder
  iii. Oral Rinse
  iv. Tooth Whiteners
  v. Denture Adhesive e) Health Care Devices
  i. Dental Floss
  ii. Toothbrushes
  iii. Respirators
  iv. Scented/flavored condoms f) Feminine Hygiene Products such as Tampons, Feminine Napkins and Wipes, and Pantiliners g) Personal Care Products: Cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a PIT emulsion, a Pickering emulsion, a micro-emulsion or nano-emulsion; and emulsions which are particularly preferred are of the "oil-in-water" (O/W) type or water-in-oil-in-water (W/O/W) type. More specifically,
i. Personal Cleansers (bar soaps, body washes, and shower gels)
ii. In-shower conditioner
iii. Sunscreen ant tattoo color protection (sprays, lotions, and sticks)
iv. Insect repellants
v. Hand Sanitizer
vi. Antiinflammatory balms, ointments, and sprays
vii. Antibacterial ointments and creams
viii. Sensates
ix. Deodorants and Antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deodorant
x. Wax-based Deodorant. An exemplary formulation as follows:
  1. Parafin Wax 10-20%
  2. Hydrocarbon Wax 5-10%
  3. White Petrolatum 10-15%
  4. Acetylated Lanolin Alcohol 2-4%
  5. Diisopropyl Adipate 4-8%
  6. Mineral Oil 40-60%
  7. Preservative (as needed)
     The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.
xi. Glycol/Soap Type Deodorant. An exemplary formulation as follows:
  1. Propylene Glycol 60-70%
  2. Sodium Stearate 5-10%
  3. Distilled Water 20-30%
  4. 2,4,4-Trichloro-2'-Hydroxy Diphenyl Ether, manufactured by the Ciba-Geigy Chemical Company and a Trademark of the Ciba-Geigy Chemical Company) 0.01-0.5%
     The ingredients are combined and heated to 75° C. with stirring until the sodium stearate has dissolved. The resulting mixture is cooled to 40° C. followed by addition of a composition of this invention.
xii. Lotion including body lotion, facial lotion, and hand lotion
xiii. Body powder and foot powder
xiv. Toiletries
xv. Body Spray
xvi. Shave cream and male grooming products
xvii. Bath Soak
xviii. Exfoliating Scrub h) Personal Care Devices
  i. Facial Tissues
  ii. Cleansing wipes
i) Hair Care Products
  i. Shampoos (liquid and dry powder)
  ii. Hair Conditioners (Rinse-out conditioners, leave-in conditioners, and cleansing conditioners)
  iii. Hair Rinses
  iv. Hair Refreshers
  v. Hair perfumes
  vi. Hair straightening products
  vii. Hair styling products, Hair Fixative and styling aids
  viii. Hair combing creams
  ix. Hair wax
  x. Hair foam, hair gel, nonaerosol pump spray
  xi. Hair Bleaches, Dyes and Colorants
  xii. Perming agents
  xiii. Hair wipes
j) Beauty Care
  i. Fine Fragrance—Alcoholic. Compositions and methods for incorporating fragrance capsules into alcoholic fine fragrances are described in U.S. Pat. No. 4,428,869. Alcoholic fine fragrances may contain the following:
    1. Ethanol (1-99%)
    2. Water (0-99%)
    3. A suspending aide including but not limited to: hydroxypropyl cellulose, ethyl cellulose, silica, microcrystalline cellulose, carrageenan, propylene glycol alginate, methyl cellulose, sodium carboxymethyl cellulose or xanthan gum (0.1%)
    4. Optionally an emulsifier or an emollient may be included including but not limited to those listed above
  ii. Solid Perfume
  iii. Lipstick/lip balm
  iv. Make-up cleanser
  v. Skin care cosmetic such as foundation, pack, sunscreen, skin lotion, milky lotion, skin cream, emollients, skin whitening
  vi. Make-up cosmetic including manicure, mascara, eyeliner, eye shadow, liquid foundation, powder foundation, lipstick and cheek rouge
k) Consumer goods packaging such as fragranced cartons, fragranced plastic bottles/boxes
l) Pet care products
  i. Cat litter
  ii. Flea and tick treatment products
  iii. Pet grooming products
  iv. Pet shampoos
  v. Pet toys, treats, and chewables
  vi. Pet training pads
  vii. Pet carriers and crates
m) Confectionaries confectionery, preferably selected from the group consisting of chocolate, chocolate bar products, other products in bar form, fruit gums, hard and soft caramels and chewing gum
  i. Gum
    1. Gum base (natural latex chicle gum, most current chewing gum bases also presently include elastomers, such as polyvinylacetate (PVA), polyethylene, (low or medium molecular weight) polyisobutene (PIB), polybutadiene, isobutene-isoprene copolymers (butyl rubber), polyvinylethylether (PVE), polyvinylbutyether, copolymers of vinyl esters and vinyl ethers, styrene-butadiene copolymers (styrene-butadiene rubber, SBR), or vinyl elastomers, for example based on vinylacetate/vinyllaurate, vinylacetate/vinylstearate or ethylene/vinylacetate, as well as mixtures of the mentioned elastomers, as described for example in EP 0 242 325, U.S. Pat. Nos. 4,518,615, 5,093,136, 5,266,336, 5,601,858 or 6,986,709) 20-25%
2. Powdered sugar 45-50%
3. glucose 15-17%
4. starch syrup 10-13%
5. plasticizer 0.1%
6. flavor 0.8-1.2%
   The components described above were kneaded by a kneader according to the foregoing formulation to provide a chewing gum. Encapsulated Flavor or sensate is then added and blended till homogeneous.
ii. Breath Fresheners
iii. Orally Dissolvable Strips
iv. Chewable Candy
v. Hard Candy n) Baked products, preferably selected from the group consisting of bread, dry biscuits, cakes and other cookies;

o) snack foods, preferably selected from the group consisting of baked or fried potato chips or potato dough products, bread dough products and corn or peanut-based extrudates;
i. Potato, tortilla, vegetable or multigrain chips
ii. Popcorn
iii. Pretzels
iv. Extruded stacks p) Cereal Products preferably selected from the group consisting of breakfast cereals, muesli bars and precooked finished rice products q) Alcoholic and non-alcoholic beverages, preferably selected from the group consisting of coffee, tea, wine, beverages containing wine, beer, beverages containing beer, liqueurs, schnapps, brandies, sodas containing fruit, isotonic beverages, soft drinks, nectars, fruit and vegetable juices and fruit or vegetable preparations; instant beverages, preferably selected from the group consisting of instant cocoa beverages, instant tea beverages and instant coffee beverages
i. Ready to drink liquid drinks
ii. Liquid Drink Concentrates
iii. Powder Drinks
iv. Coffee: Instant Cappuccino
   1. Sugar 30-40%
   2. Milk Powder 24-35%
   3. Soluble Coffee 20-25%
   4. Lactose 1-15%
   5. Food Grade Emulsifier 1-3%
   6. Encapsulated Volatile Flavor 0.01-0.5%
v. Tea
vi. Alcoholic r) Spice blends and consumer prepared foods
i. Powder gravy, sauce mixes
ii. Condiments
iii. Fermented Products s) Ready to heat foods: ready meals and soups, preferably selected from the group consisting of powdered soups, instant soups, precooked soups
i. Soups
ii. Sauces
iii. Stews
iv. Frozen entrees t) Dairy Products milk products, preferably selected from the group consisting of milk beverages, ice milk, yogurt, kefir, cream cheese, soft cheese, hard cheese, powdered milk, whey, butter, buttermilk and partially or fully hydrolyzed milk protein-containing products Flavored milk beverages
i. Yoghurt
ii. Ice cream
iii. Bean Curd
iv. Cheese u) Soya protein or other soybean fractions, preferably selected from the group consisting of soya milk and products produced therefrom, soya lecithin-containing preparations, fermented products such as tofu or tempeh or products produced therefrom and soy sauces;

v) Meat products, preferably selected from the group consisting of ham, fresh or raw sausage preparations, and seasoned or marinated fresh or salt meat products w) Eggs or egg products, preferably selected from the group consisting of dried egg, egg white and egg yolk x) Oil-based products or emulsions thereof, preferably selected from the group consisting of mayonnaise, remoulade, dressings and seasoning preparations y) fruit preparations, preferably selected from the group consisting of jams, sorbets, fruit sauces and fruit fillings; vegetable preparations, preferably selected from the group consisting of ketchup, sauces, dried vegetables, deep-frozen vegetables, precooked vegetables, vegetables in vinegar and preserved vegetables z) Flavored pet foods.

The above-listed applications are all well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid laundry detergents include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Liquid dish detergents are described in U.S. Pat. Nos. 6,069,122 and 5,990,065. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Automatic Dish Detergents are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The terms "include," "includes," and "including," are meant to be non-limiting.

The terms "capsule" and "microcapsule" herein are used interchangeably.

The terms "polyfunctional isocyanate," "multifunctional isocyanate," and "polyisocyanate" are used interchangeably and refer to a compound having two or more isocyanate (—NCO) groups.

The terms "polyfunctional amine," "multifunctional amine," and "polyamine" are used interchangeably and refer to a compound containing one, two, or more primary or secondary amine groups. These terms also refers to a compound containing one or more primary/secondary amine groups and one or more hydroxyl groups (—OH).

The terms "polyethyleneimine," "polyethyleneimines," "polyethylenimine," and "polyethylenimines" are used interchangeably.

The terms "polyfunctional alcohol," "multifunctional alcohol," "poly alcohol," and "polyol" are used interchangeably and refer to a compound having two or more hydroxyl groups.

The term "degree of polymerization" refers to the number of repeat units in a polymer.

The term "degree of crosslinking" refers to percent of interconnecting units over the total repeat unit. It is generally measured by swelling experiments. See ASTM Standard Test Method ASTM D2765-11; Lange, Colloid & Polymer Science 264, 488-93 (1986).

The terms "multi-functional nucleophile" and "polyfunctional nucleophile" are used herein interchangeably. They both refer to an aliphatic or aromatic hydrocarbon onto which is attached two or more nucleophilic groups such as primary/secondary amine groups and the hydroxyl group.

The term "multi-functional electrophile" and "polyfunctional electrophile" are used interchangeably and refer to an aliphatic or aromatic hydrocarbon, onto which is attached two or more electrophilic groups reactive towards the nucleophilic group. Examples of an electrophilic group include: aldehydes, halide, sulfate esters, sulphonate esters, epoxide, chlorohydrins as well as terminal olefins conjugated with a carbonyl group including ketone, amide, or ester.

The term "curing" as used polymer chemistry and process engineering refers to a toughening or hardening process of a polymer by cross-linking of polymer chains, brought about by heat, chemical additives, or light radiation.

The invention is described in greater detail by the following non-limiting examples. Without further elaboration, it is believed that one skilled in the art can, based on the description herein, utilize the present invention to its fullest extent. All publications cited herein are incorporated by reference in their entirety.

Example 1: Guar Microcapsule Composition 1

An aqueous solution was prepared that contained 0.5% sodium polystyrene sulfonate (commercially available under the tradename of Flexan® II from AkzoNobel Surface Chemistry, Bridgewater, New Jersey), a 1% octenyl succinic anhydride (OSA)-modified starch (commercially available under the tradename of Purity Gum® Ultra from Ingredion, Bridgewater, New Jersey), a 3% cationic guar solution (commercially available under the tradename of Aquacat™ CG518 from Ashland, Covington, Kentucky) in water. An oil solution was prepared that contained 1% of trimethylolpropane adduct of xylylenediisocyanate (commercially available under the tradename of Takenate™ D110N from Mitsui Chemical, Indianapolis, Indiana), 32% of a model fragrance (IFF, Union Beach, New Jersey) and 8% of a caprylic/capric triglyceride (Neobee® oil commercially available from Stepan Company, Maywood, New Jersey).

The two solutions were mixed and homogenized at 7400 rpm for 3 minutes. Subsequently, 0.67% of glutaraldehyde (Sigma Aldrich, St. Louis, Missouri) was added, followed by the addition of 0.66% diluted sulfuric acid to adjust the pH of the mixture to 2. The resultant mixture was cured at 55° C. for 2 hours and then 75° C. for additional 2 hours.

Guar Microcapsule Composition 1 thus prepared contained moieties derived from 3% of a cationic guar gum, 1% polyisocyanate, and 0.67% of glutaraldehyde, each by weight of the composition.

Example 2: Guar Microcapsule Composition 2

Microcapsule Composition 2 was prepared following the procedure in Example 1 except that (i) a 0.5% cationic guar (commercially available under the trade name of N-Hance™ C261N from Ashland), was used instead of 3% Aquacat™ CG518, (ii) 0.01%, instead of 0.66%, sulfuric acid was added, and (iii) the microcapsule was cured at 55° C. for 4 hours.

Guar Microcapsule Composition 2 thus prepared contained moieties derived from 0.5% of a cationic guar gum, 1% polyisocyanate, and 0.67% of glutaraldehyde, each by weight of the composition.

Examples 3-7: Guar Microcapsule Compositions 3-7

Microcapsule Compositions 3-7 were prepared following the procedure as described in Example 1 varying the amounts of polyisocyanate, glutaraldehyde, and tannic acid or under a different pH. See Table 4 below. The microcapsules were evaluated for post-rub headspace and encapsulation efficiency. The results are shown in Table 4.

Table 4 also includes the amounts of the polyisocyanate, glutaraldehyde, and tannic acid by weight of each microcapsule composition.

Example 8: Guar Microcapsule Composition 8

Microcapsule composition 8 was prepared following the same procedure as described in Example 2 except that an underivatized guar (commercially available under the trade name Guar Gum TICOLV™ from TIC Gums Inc., White March, Maryland) was added instead of N-Hance™ C261N.

Example 9: Guar Microcapsule Composition 9

Microcapsule Composition 9 was prepared following the same procedure as described in Example 2 except that a non-ionic guar (commercially available as Jaguar® HP-8 COS from Solvay, Cranbury, New Jersey) was added instead of N-Hance™ C261N.

Example 10: Guar Microcapsule Composition 10

Microcapsule Composition 10 was prepared following the same procedure as described in Example 2 except that a underivatized guar gum (commercially available as HV-101 from AEP Colloids, Hadley, New York) was added instead of N-Hance™ C261N.

Examples 11-25

Microcapsule Compositions 11-25 were prepared following the procedure described in Example 2 with the components shown in Table 1 below.

TABLE 1

| Microcapsule Compositions | Guar Commercial Name | Guar % | Poly-isocyanate % | Glutaldehyde % | Tannic acid % |
|---|---|---|---|---|---|
| 11 | Aquacat ™ | 3 | 1 | 0.7 | 1 |
| 12 | Aquacat ™ | 3 | 1 | 0.7 | 2.5 |
| 13 | Aquacat ™ | 3 | 1 | 0.7 | 0 |
| 14 | Aquacat ™ | 1 | 1 | 0.7 | 0 |
| 15 | N-Hance ™ | 3 | 1 | 0.7 | 0 |
| 16 | N-Hance ™ | 0.5 | 1 | 0.7 | 0 |
| 17 | Jaguar ® C14S (Solvay) | 0.5 | 1 | 0.7 | 0 |
| 18 | Dehyquart ® (BASF) | 0.5 | 1 | 0.7 | 0 |
| 19 | N-Hance ™ | 2 | 1 | 0 | 1 |
| 20 | N-Hance ™ | 1 | 1 | 0 | 1 |
| 21 | Jaguar ® C14S | 0.5 | 1 | 0 | 1 |
| 22 | JK-141 (Jingkun) | 2 | 1 | 0 | 1 |
| 23 | Jaguar ® HP | 0.5 | 1 | 0.7 | 0 |
| 24 | HV-101 (AEP Colloids) | 0.5 | 1 | 0.7 | 0 |
| 25 | TICOLV ™ (TIC Gum) | 0.5 | 1 | 0.7 | 0 |
| 26 | Aquacat ™ | 3 | 1 | 0.3 | 0 |
| 27 | Aquacat ™ | 3 | 1 | 0.1 | 0 |
| 28 | N-Hance ™ | 1 | 1 | 0 | 1 |
| 29 | N-Hance ™ | 1 | 1 | 0 | 1.8 |
| 30 | Aquacat ™ | 3 | 0.8 | 0.7 | 0 |
| 31 | Aquacat ™ | 3 | 0.6 | 0.7 | 0 |

Example 1C: Post Addition of Guar after Formation of the Emulsion

The capsule was prepared following the same procedure as in Example 3 except that (i) a sodium salt of naphthalene sulfonate condensate (commercially available as Morwet® D-425 from AkzoNobel) was used instead of Flexan® II and (ii) 3% Aquacat™ CG518 was added after the homogenization process instead of in the aqueous solution before the emulsifying step.

Example 2C

Microcapsule 2C was prepared following the procedure described in Example 2 except that glutaraldehyde was not added to the reaction mixture.

Sensory Performance Evaluation

The microcapsules prepared above were used in a fabric conditioner application and evaluated for their fragrance intensity in a LMS scale of 0 to 30, in which a score of 1 indicates a weak smell, a score of 5 indicates an intermediate smell and a score of 15 indicates a strong smell. Each microcapsule was incorporated into a model un-fragranced fabric conditioner base at 0.6% neat oil equivalence. The results are shown in Tables 2-4 below.

Encapsulation Efficiency

Encapsulation efficiency (EE) was calculated as: EE=[1−(Free oil/Total Oil)]×100%. The free oil and total oil analysis were performed following the methods described on page 21 of WO 2017/161364. The results are shown in Tables 2-4 below.

Post-Rub Headspace

Microcapsules of this invention were also evaluated using headspace on a Tenax tube, in which the fragrance intensities were measured in ppb. The washed and dried towel was put in a plastic bag, sealed and rubbed. The headspace was collected through a nozzle.

A batch of fabric conditioners were prepared using the microcapsule compositions described in Examples 2 and 2C.

The fabric conditioners were then evaluated for their encapsulation efficiency (EE) and fragrance intensity post rub after washing and drying towels using the conditioners. The results are shown in Table 2 below.

TABLE 2

| Example | polyisocyanate | glutaraldehyde | Post-Rub Intensity | EE |
|---|---|---|---|---|
| 2 | 1% | 0.67% | 6.2 | 99.4% |
| 2C | 1% | 0% | 0.7 | 91.5% |

A second batch of fabric conditioners were prepared using the microcapsule compositions described in Examples 1 and 2 and also the model fragrance as a free fragrance oil without encapsulation. The three fabric conditioners were evaluated right after washing and drying (T=0) and also after being stored for 4 weeks since washing and drying. See Table 3.

TABLE 3

| Example | Post-Rub Intensity T = 0 | Post-Rub Intensity T = 4 weeks | EE |
|---|---|---|---|
| 1 | 11.2 | 9.3 | 99.7% |
| 2 | 10.9 | 7.9 | 99.4% |
| Free Fragrance | 4.5 | 5.5 | — |

A third batch of fabric conditioners were evaluated using the microcapsule compositions shown in Table 4 below.

TABLE 4

| Example | Poly-isocyanate | pH | Glutaraldehyde | Tannic Acid | Post-Rub Headspace (ppb) | EE |
|---|---|---|---|---|---|---|
| 1 | 1% | 2 | 0.67% | 0% | 2371 | 99.7% |
| 3 | 1% | 6 | 0.67% | 0% | 2260 | 99.7% |
| 4 | 0.8% | 2 | 0.67% | 0% | 1315 | 99.7% |
| 5 | 0.6% | 2 | 0.67% | 0% | 1046 | 99.4% |
| 6 | 1% | 2 | 0.67% | 2.5% | 2301 | 99.7% |
| 7 | 1% | 2 | 0% | 2.5% | 1874 | 99.7% |
| 8 | 1% | 2 | 0.67% | 0% | 1195.7 | 99.4% |
| 9 | 1% | 2 | 0.67% | 0% | 1509.7 | 99.7% |
| 10 | 1% | 2 | 0.67% | 0% | 1463 | 97.5% |
| 1C | 1% | 2 | 0.67% | 0% | 288.7 | 99.3% |
| Free fragrance | — | — | — | — | 43.3 | — |

Comparative Compositions 3C-5C Without Guar Gum

Comparative Compositions 4C-6C were prepared following the procedure described in Example 2 without guar gum. Table 5 below shows the components and readings from the headspace gas chromatography at the post-rub stage.

TABLE 5

| Example | Takenate ™ % | Glutaraldehyde % | Tannic acid | Post-Rub (analytical)* |
|---|---|---|---|---|
| 3C | 1 | 0.7 | 0 | 114 |
| 4C | 1 | 0.7 | 2.5 | 292 |
| 5C | 1 | 0.3 | 2.5 | 443 |

Comparative Compositions 6C-8C Without Polyisocyanate

Comparative Compositions 6C-8C were prepared following the procedure described in Example 2 without polyisocyanate. Table 6 below shows the components, free oil %, and post-rub fragrance intensity score from a sensory evaluation.

TABLE 6

| Example | Guar | Guar % | Glutaraldehyde % | Free Oil % | Post-Rub (sensory)* |
|---|---|---|---|---|---|
| 6C | Aquacat ™ | 4 | 0.7 | 9.6 | 2 |
| 7C | Aquacat ™ | 2 | 0.7 | 9.2 | 2.2 |
| 8C | N-Hance ™ | 0.5 | 0.7 | 13.3 | 1.8 |

Comparative Composition 9C Without Glutaldehyde and Tannic Acid

Comparative Composition 9C was prepared following the procedure described in Example 2 without glutaldehyde and tannic acid. The composition was prepared using 0.5% N-Hance™ and 1% Takenate™ D-110N. The post-rub fragrance intensity was only 0.7 as evaluated by the sensory performance study described above.

Compositions 3, and 26-29 with Various Amount of Glutaldehyde and Tannic Acid

Free oil and post-rub headspace GC readings were summarized in Table 7 below.

TABLE 7

| Example | Guar Name | Guar % | Takenate ™ % | Glutaraldehyde % | Tannic acid | Free Oil % | Post-Rub |
|---|---|---|---|---|---|---|---|
| 3 | Aquacat ™ | 3 | 1 | 0.7 | 0 | 0.1 | 1812 |
| 26 | Aquacat ™ | 3 | 1 | 0.3 | 0 | 0.1 | 1307 |
| 27 | Aquacat ™ | 3 | 1 | 0.1 | 0 | 0.2 | 686 |
| 28 | N-Hance ™ | 1 | 1 | 0 | 1 | <0.1 | 2031 |
| 29 | N-Hance ™ | 1 | 1 | 0 | 1.8 | <0.1 | 2016 |

Compositions 3, 30-31, 17, and Comparative Compositions 10C and 11C with Various Amount of Polyisocyanate and Glutaraldehyde Comparative Compositions 10C and 11C were prepared following the same procedure as Composition 3 with different amount of the polyisocyanate and glutaraldehyde. Free oil and post-rub headspace GC readings were summarized in Table 8 below.

TABLE 8

| Example | Guar Name | Guar % | Takenate ™ % | Glutaraldehyde % | Tannic acid % | Free Oil % | Post-Rub |
|---|---|---|---|---|---|---|---|
| 3 | Aquacat ™ | 3 | 1 | 0.7 | 0 | <0.1 | 2046 |
| 30 | Aquacat ™ | 3 | 0.8 | 0.7 | 0 | 0.1 | 1315 |
| 31 | Aquacat ™ | 3 | 0.6 | 0.7 | 0 | 0.2 | 1046 |
| 27 | Aquacat ™ | 3 | 1 | 0.1 | 0 | <0.1 | 1737 |
| 10C | Aquacat ™ | 3 | 0.8 | 0.1 | 0 | 0.4 | 48 |
| 11C | Aquacat ™ | 3 | 0.6 | 0.1 | 0 | 1 | 41 |

Compositions 13, 23, 32, 33, and Comparative Composition 12C with pH Adjustment

Compositions 13, 23, 32, 33, and Comparative Composition 12C were prepared with 3% Aquacat™ and 1% Takenate™ D-110N under different pH. Free oil and post-rub headspace GC readings were summarized in Table 9 below.

TABLE 9

| Example | pH | Glutaraldehyde % | Tannic acid % | Free Oil % | Post-Rub |
|---|---|---|---|---|---|
| 23 | 3 | 0.7 | 0 | <0.1 | 2210 |
| 32 | 7 | 0.7 | 0 | <0.1 | 2251 |
| 12C | 9 | 0.7 | 0 | <0.1 | 140 |
| 13 | 3 | 0.7 | 2.5 | <0.1 | 1777 |
| 33 | 7 | 0.7 | 2.5 | 0.1 | 2081 |

Comparative Composition 13C and 14C

Comparative Composition 13C and 14C were prepared by adding guar gum to the oil-in-water emulsion instead of adding it before the emulsion. Free oil and post-rub evaluation were summarized in Table 10 below.

TABLE 10

| Example | Guar | Takenate ™ % | Glutaraldehyde % | Tannic acid % | Free Oil % | Post-Rub |
|---|---|---|---|---|---|---|
| 13C | Aquacat ™ 4% | 1 | 0.1 | 0 | 0.2 | 288[1] |
| 14C | N-Hance ™ 0.5% | 1 | 0.7 | 0 | 14.9 | 0.8[2] |

[1]Headspace GC reading
[2]Fragrance intensity in sensory evaluation

Performance in Hair Conditioners

Compositions 13, 20, and 23-25 were added to a unfragranced hair conditioner base and a shampoo base at a fragrance dosage of 0.25%.

The hair conditioner base contained 4% of fatty alcohol, 0.7% of behentrimonium chloride, 1% of terminal amino silicones, 2.5% of silicone, 0.5% of preservative, and water.

The shampoo base contained 12% of sodium lauryl ether sulphate, 1.6% of cocamidopropyl betaine, 0.2% of nonionic guar gum, 2%-3% of silicone, 0.5% of preservative, and water.

Hair swatches were evaluated after brush with a fragrance intensity scale from 0 to 10 after washing with the hair conditioner or shampoo. The results were shown in Table 11 below.

TABLE 11

| Example | Hair Conditioner | Shampoo |
|---|---|---|
| 13 | 5 | 5.8 |
| 20 | 3.1 | 7.3 |
| 23 | 5 | 5 |
| 24 | 4 | 2 |
| 25 | 3.5 | 2.5 |

To improve deposition of the encapsulated fragrance, the microcapsule was coated with chitosan as follows. A 3% chitosan (extracted from fungal) aqueous solution was prepared by dissolving chitosan in water together with 1% of acetic acid. Composition 25 was mixed with a diluted sulfuric acid solution until the pH reached 2. The chitosan solution was added to the acidified Composition 25 so that the chitosan was present at a level of 2%. The resultant microcapsule composition had a pH of 2 and was heated to a temperature of 60° C. and kept at that temperature for 4 hours to obtain Microcapsule Composition 35 of this invention.

Microcapsule Composition 35 was mixed with 0.25 wt % of the copolymer of acrylamide and acrylamidopropyltrimonium chloride or the copolymer of acrylamide and methacrylamidopropyl-trimonium chloride to obtain Microcapsule Compositions 36 and 37.

Microcapsule Composition 35 was incorporated into a hair conditioner base and evaluated as described above. It showed a fragrance intensity of 5.2.

Reaction Confirmation

To confirm the reaction between a guar and glutaraldehyde, a mixture was prepared by adding 10 parts of 1-10% a guar aqueous solution and 1 part of 50% glutaraldehyde aqueous solution, followed by adjusting the pH of the mixture to pH 2 with a concentrated sulfuric acid aqueous solution. The mixture was cured at 55° C. for 16 hours.

A guar is commercially available, for example, under the tradenames of N-Hance™ C261N, N-Hance™ BF-13, N-Hance™ CG13, Aquacat™ CG518, Aquacat™ PF618, Dehyquart® Guar HP, Dehyquart® Guar N, and Dehyquart® Guar TC. These commercial guars were used in the above evaluation.

The above mixture was turned into a transparent to semi-transparent solid gel. The gel was analyzed with nuclear magnetic resonance spectroscopy (NMR). The formation of acetal and hemi-acetal was confirmed by NMR. Not to be bounded by any theory, it is believed that the hydroxyl groups (—OH) in the guar react with the formyl groups (—CHO) in the glutaraldehyde under the acidic condition (e.g., pH 1 to 6). This crosslinking reaction contributes to the formation of the shell of the microcapsule.

In addition, the acetal and semi-acetal was further crosslinked with an isocyanate or tannic acid, when present. These further crosslinking reactions reinforce the microcapsule wall and improve the encapsulation efficiency.

The microcapsule surface is analyzed using X-ray Photoelectron Spectroscopy (XPS) and solid-state NMR to confirm the formation of polyurethane, polyimine, acetal, and hemiacetal in the microcapsule wall.

Consumer Product Examples

Microcapsule compositions of this invention can be added to various consumer products. Non-limiting examples are shown in Table 12 below.

TABLE 12

| Fabric Softener | Antiperspirant (AP) roll-on product |
|---|---|
| Microcapsule Composition, 0.1-2% NOE[2] | Microcapsule Composition, 0.1-2% NOE |
| Quat surfactant (active), 1-20% | Anionic surfactant, 1-3% |
| Stabilizer, <1% | Aluminum chlorohydrate, 10-20%, |
| pH buffer, <1% | Silica, less than 1% |
| Salt, <1% | Helianthus annuus, 1-2% |
| Preservative, <0.1% | Water, q.s. to 100% |
| Antifoam, <0.1 | |
| Water, q.s. to 100% | |

| Shampoo | Hair conditioner |
|---|---|
| Microcapsule Composition, 0.1-2% NOE | Microcapsule Composition, 0.1-2% NOE |
| Sodium lauryl ether sulphate, 12% | Fatty alcohol, 4% |
| Cocamidopropyl betaine, 1.6% | Behentrimonium chloride, 0.7% |
| Non-ionic guar, 0.2% | Terminal amino silicones, 1% |
| Silicone, 2-3% | Silicone, 2.5% |
| Preservative, 0.5% | Preservative, 0.5% |
| Water, q.s. to 100% | Water, q.s. to 100% |

| Powder detergent Example 1 | Powder detergent Example 2 |
|---|---|
| Microcapsule Composition, 0.1-2% NOE | Microcapsule Composition, 0.1-2% NOE |
| Sodium Carbonate, 81.9% | Sodium alkl benzene sulphonate, 7.6% |
| Ethoxylated $C_{12}$-$C_{15}$ alcohol sulfate salt, 4.3% | Nonionic surfactant, 9.8% |
| $C_{12}$-$C_{15}$ alcohol ethoxylate, 2.4% | Soap, 1.7% |
| Sodium Sulfate, 1.5% | sodium aluminosilicate (zeolite), 27% |
| Sodium bicarbonate, 1.3% | Sodium Carbonate, 13% |
| Sodium polyacrylate, 0.7% | Alkaline sodium silicate (1:3.3), 0.5% |
| Sodium Carboxymethylcellulose, 0.1% | CP5-polymer ex BASF, 4% |
| Optical Brightener, 0.2% | Sodium Carboxymethylcellulose (SCMC), 0.6% |
| Polyvinyl Alcohol, 0.1% | Water, 11% |
| Water, 7.4% | Minors, 1.5% |
| | Dry Additives |
| | Sodium perborate monohydrate (PBM), 14% |
| | Enzyme, 1.1% |
| | TAED granules (83%), 7.4% |
| | Ethylene diamine tetramethylene phosphonate (EDTMP), 0.4% |
| | anti-foam granules, 0.4% |

| Powder detergent Example 3 | Roll on deodorant |
|---|---|
| Microcapsule Composition, 0.1-2% NOE | Microcapsule Composition, 0.1-2% NOE |
| Zeolite, 36.6-45.9% | Aluminum Chlorohydrate 50% Solution, 30-34% |
| Sodium carbonate, 13.3-16.6% | Steareth-20, 1.3-1.9% |
| Soap, 0-0.7% | Steareth-2, 5-5.6% |
| Sodium sulphate, 0-2% | Silica, 0.5-1.1% |
| Sodium Carboxymethylcellulose (SCMC), 0-0.9% | Preservative, 0.7-1.3% |
| Fluorescer, 0-0.7% | |
| Sodium alkyl benzene sulphonate, | |

TABLE 12-continued 0-23.3%
Primary Alkyl sulphate, 0-23.1%
Nonionic 7 EO surfactant, 0-4.1%
Nonionic 3 EO surfactant, 0-7%
CP5 co-polymer ex BASF, 1-3%
Alkaline Sodium silicate, 0-4%
Water, 11.5-15.8%

Liquid detergent

Microcapsule Composition, 0.1-2% NOE
A non-soap surfactant (anionic or
nonionic) with a range of 15 wt. % to 45
wt. %, preferably 32 wt. % to 35 wt. %
Propylene glycol, 0.5-50%, preferably
10-20%
One or more soil release polymer (SRP)
that can be between 0.01% and 10%,
preferably 0.9% and 2.5%,
Water, 5-35%, preferably 15-25%

[1]All component percentages are shown by weight of the consumer product.
[2]NOE is the neat fragrance oil equivalence which equals to the weight percentage of the fragrance oil in the consumer product.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of encapsulating an active material, one skilled in the art can design and prepare a capsule composition by using different encapsulating polymers, coatings, guar gum, and/or capsule formation aids, varying the concentrations of these wall-forming materials and/or catalysts to achieve desirable organoleptic or release profiles in a consumable product. Further, the ratios among the wall forming materials, capsule forming aids, adjuvants, core modifiers, active materials, and catalysts can also be determined by a skilled artisan through assays known in the art to prepare capsule compositions with desirable properties.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A microcapsule composition comprising microcapsules that contain a microcapsule core and a microcapsule shell encapsulating the microcapsule core, wherein
   the microcapsule core contains an active material, and
   the microcapsule shell comprises a polygalactomannan crosslinked with a multi-functional aldehyde and a polyisocyanate,
   wherein the polygalactomannan is covalently bonded to the multi-functional aldehyde via one or more acetal or hemiacetal bonds; and
   wherein the microcapsule shell does not contain a polyamine.

2. The microcapsule composition of claim 1, wherein the multi-functional aldehyde comprises glutaraldehyde, glyoxal, di-aldehyde starch, malonaldehyde, or genipin.

3. The microcapsule composition of claim 1, wherein the microcapsule shell further comprises tannic acid.

4. The microcapsule composition of claim 1, wherein the polyisocyanate is present at a level of 0.5% to 3.5% by weight of the microcapsule composition.

5. The microcapsule composition of claim 1, wherein the polygalactomannan is present at a level of 1% to 3% by weight of the microcapsule composition.

6. The microcapsule composition of claim 1, wherein said microcapsule composition further comprise a deposition polymer.

7. A consumer product comprising the microcapsule composition of claim 1.

8. A method of preparing the microcapsule composition of claim 1, comprising the steps of:
   (a) emulsifying an aqueous phase comprising a polygalactomannan with an oil phase comprising a polyisocyanate and an active material thereby forming an oil-in-water emulsion,
   (b) adding a multi-functional aldehyde to the oil-in-water emulsion, and
   (c) adjusting the pH of the oil-in-water emulsion to 7 or less so as to form microcapsules that contain a microcapsule core and a microcapsule shell encapsulating the microcapsule core,
   wherein the microcapsule core contains the active material, and the microcapsule shell comprises the polygalactomannan crosslinked with the multi-functional aldehyde and the polyisocyanate;
   wherein the polygalactomannan is covalently bonded to the multi-functional aldehyde via one or more acetal or hemiacetal bonds; and
   wherein the microcapsule shell does not contain a polyamine.

9. The microcapsule composition of claim 1, wherein the polygalactomannan is selected from the group of a cationic guar gum, a native guar gum, a hydroxypropyl guar gum, guar hydroxypropyltrimonium chloride, and combinations thereof.

10. The method of claim 8, wherein the polygalactomannan is selected from the group of a cationic guar gum, a native guar gum, a hydroxypropyl guar gum, guar hydroxypropyltrimonium chloride, and combinations thereof.

11. The microcapsule composition of claim 1, wherein the active material is selected from the group of flavors, fragrances, malodor counteracting agents, and combination thereof.

12. The microcapsule composition of claim 1, wherein the polygalactomannan is guar gum, the weight ratio between the guar gum and the multi-functional aldehyde is 60:1 to 3:10, and the microcapsule composition does not contain alginate.

13. The microcapsule composition of claim 1, wherein the polyisocyanate is an aromatic polyisocyanate selected from the group of a polyisocyanurate of toluene diisocyanate, a trimethylol propane-adduct of toluene diisocyanate, a trimethylol propane-adduct of xylylene diisocyanate, and combinations thereof.

* * * * *